United States Patent [19]

Kittrell et al.

[11] Patent Number: 5,290,275

[45] Date of Patent: Mar. 1, 1994

[54] CATHETER FOR LASER ANGIOSURGERY

[75] Inventors: Carter Kittrell, Houston, Tex.; Robert M. Cothren, Jr., Cleveland, Ohio; Michael S. Feld, Waban; Barry Sachs, Newton, both of Mass.

[73] Assignee: Massachusetts Institute of Technology, Cambridge, Mass.

[21] Appl. No.: 731,010

[22] Filed: Jul. 16, 1991

Related U.S. Application Data

[60] Continuation of Ser. No. 411,326, Sep. 22, 1989, Pat. No. 5,034,010, which is a division of Ser. No. 58,675, May 26, 1987, Pat. No. 4,913,142, which is a continuation of Ser. No. 715,239, Mar. 22, 1985, abandoned.

[51] Int. Cl.$^5$ ............................................. A61B 17/32
[52] U.S. Cl. ............................................. 606/15
[58] Field of Search ............................ 128/395–398; 606/7, 13–17

[56] References Cited

U.S. PATENT DOCUMENTS

| | | |
|---|---|---|
| 3,315,680 | 4/1967 | Silbertrust et al. . |
| 3,327,117 | 6/1967 | Kamentsky . |
| 3,327,119 | 6/1967 | Kamentsky . |
| 3,417,745 | 12/1968 | Sheldon ............... 128/6 |
| 3,461,856 | 8/1969 | Polanyi . |
| 3,467,098 | 11/1969 | Ayres . |
| 3,471,215 | 10/1969 | Snitzer . |
| 3,647,299 | 3/1972 | Lavaliee ............... 356/41 |
| 3,690,769 | 9/1972 | Mori ............... 356/41 |
| 3,858,577 | 1/1975 | Bass et al. ............... 128/398 |
| 3,865,113 | 2/1975 | Sharon et al. ............... 128/395 |
| 3,866,599 | 2/1975 | Johnson ............... 128/6 |
| 4,040,413 | 8/1977 | Ohshiro ............... 128/6 |
| 4,072,147 | 2/1978 | Hett ............... 128/6 |
| 4,120,293 | 10/1978 | Muckerheide ............... 128/395 |
| 4,141,362 | 2/1979 | Wurster ............... 128/395 |
| 4,146,019 | 3/1979 | Bass et al. ............... 128/6 |
| 4,169,464 | 10/1979 | Obrez ............... 128/657 |
| 4,207,874 | 6/1980 | Choy ............... 128/6 |
| 4,266,548 | 5/1981 | Davi . |
| 4,273,109 | 6/1981 | Enderby ............... 128/6 |
| 4,292,961 | 10/1981 | Kawashima ............... 128/6 |
| 4,295,470 | 10/1981 | Shaw et al. ............... 128/634 |
| 4,313,431 | 2/1982 | Frank ............... 128/7 |
| 4,409,993 | 10/1983 | Furihata ............... 128/784 |
| 4,418,688 | 12/1983 | Loeb ............... 128/6 |
| 4,421,382 | 12/1983 | Doi et al. . |
| 4,445,892 | 5/1984 | Hussein et al. ............... 128/4 |

(List continued on next page.)

FOREIGN PATENT DOCUMENTS

| | | |
|---|---|---|
| 2826383 | 6/1978 | Fed. Rep. of Germany . |
| 82/01669 | 11/1982 | PCT Int'l Appl. . |
| 84/00474 | 2/1984 | PCT Int'l Appl. . |
| 8500510 | 2/1985 | World Int. Prop. O. . |

OTHER PUBLICATIONS

Grady, "The Artery Zapper", (Dec. 1982).
Ginsburg, et al., *Clin. Cardiol.*, 7:54–58 (1984).
Rawls, *Science*, pp. 14–15 (Mar. 1984).
Choy et al., *The American Journal of Cardiology*, vol. 50 (Dec. 1982) "Translumal . . . Angioplasty".
Choy et al., *The American Journal of Cardiology*, vol. 50 (Dec. 1982) "Laser Coronary in Hearts".
Abela, et al., *The American Journal of Cardiology*, vol. 50, (Dec. 1982).
Lee et al., *American Heart Journal*, vol. 103 (Jun. 1982).

*Primary Examiner*—Max Hindenburg
*Attorney, Agent, or Firm*—Hamilton, Brook, Smith & Reynolds

[57] ABSTRACT

A laser catheter is disclosed wherein optical fibers carrying laser light are mounted in a catheter for insertion into an artery to provide controlled delivery of a laser beam for percutaneous intravascular laser treatment of atherosclerotic disease. A transparent protective shield is provided at the distal end of the catheter for mechanically diplacing intravascular blood and protecting the fibers from the intravascular contents, as well as protecting the patient in the event of failure of the fiber optics. Multiple optical fibers allow the selection of tissue that is to be removed. A computer controlled system automatically aligns fibers with the laser and controls exposure time. Spectroscopic diagnostics determine what tissue is to be removed.

24 Claims, 22 Drawing Sheets

U.S. PATENT DOCUMENTS

| | | | |
|---|---|---|---|
| 4,470,407 | 9/1984 | Hussein | 128/6 |
| 4,512,762 | 4/1985 | Spears | 604/21 |
| 4,543,090 | 9/1985 | McCoy | 604/95 |
| 4,564,011 | 1/1986 | Goldman | 128/398 |
| 4,587,972 | 5/1986 | Morantte, Jr. | 128/660 |
| 4,592,353 | 6/1986 | Daikuzono . | |
| 4,627,436 | 12/1986 | Leckrone | 128/398 |
| 4,641,650 | 2/1987 | Mok | 128/6 |
| 4,641,912 | 2/1987 | Goldenberg | 128/6 |
| 4,682,596 | 7/1987 | Bales et al. . | |
| 4,686,979 | 8/1987 | Gruen et al. . | |
| 4,800,876 | 1/1989 | Fox et al. . | |

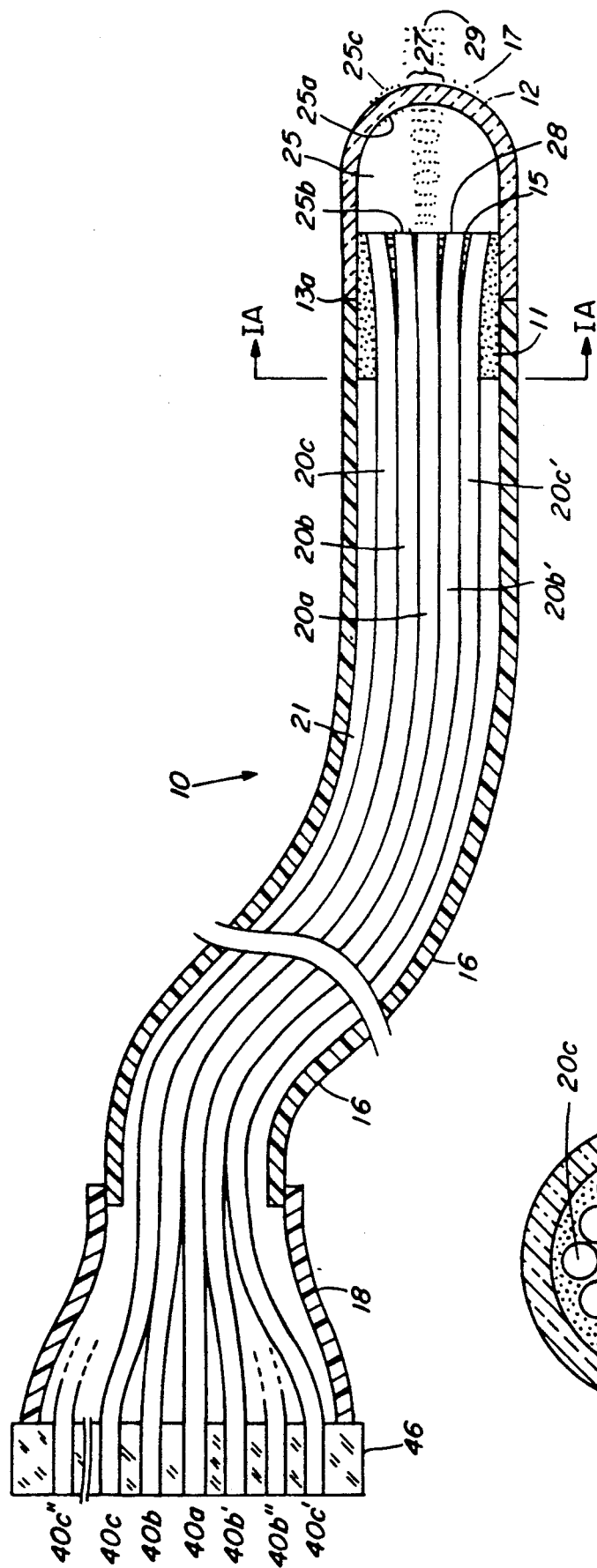
FIG. 1
FIG. 1B
FIG. 1A

FIG. 8A
PREPARE PARTS
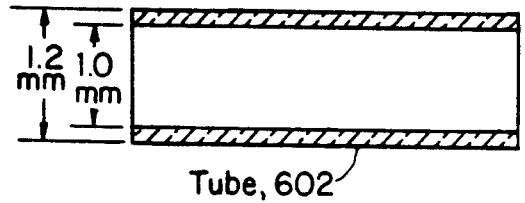
Tube, 602
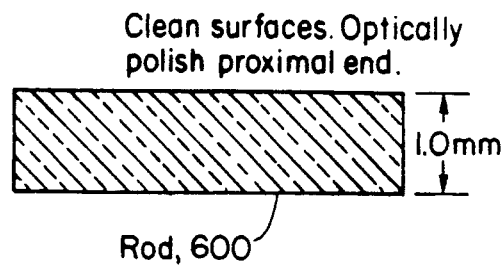
Clean surfaces. Optically polish proximal end.
Rod, 600
FIG. 8B
INSERT AND FUSE
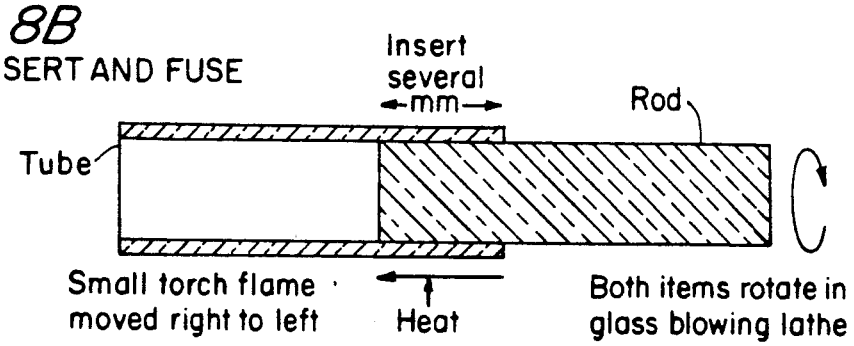
Tube
Insert several mm
Rod
Small torch flame moved right to left
Heat
Both items rotate in glass blowing lathe
FIG. 8C
CUT TO LENGTH
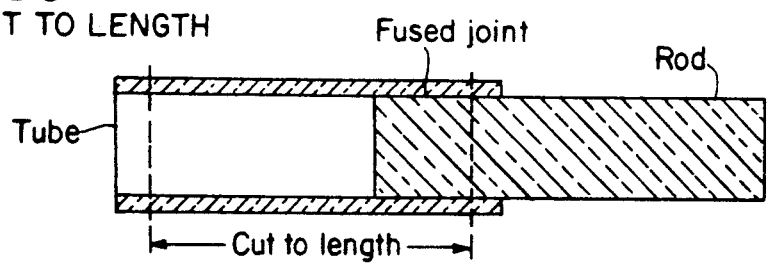
Tube
Fused joint
Rod
Cut to length
FIG. 8D
POLISH
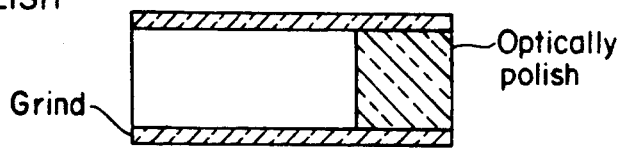
Grind
Optically polish
FIG. 8Ea
SHAPED
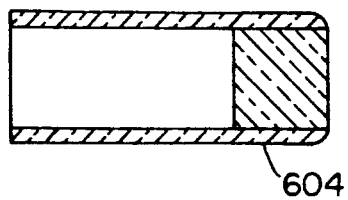
604
FIG. 8Eb
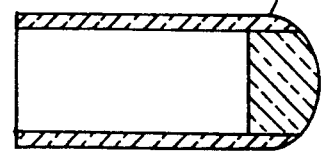
604'

BUTT END CONSTRUCTION

CONICAL CONSTRUCTION

STEP DIAMETER CONSTRUCTION

METAL BAND SUPPORT

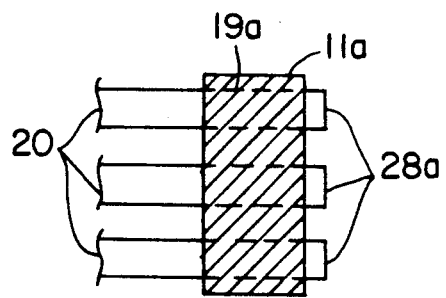
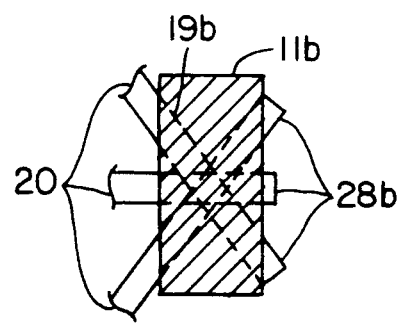
FIG. 10A  FIG. 10B
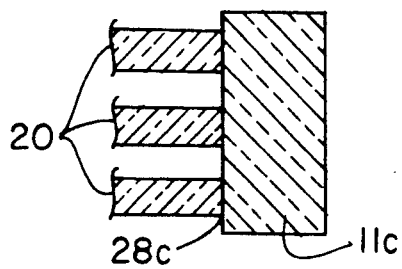
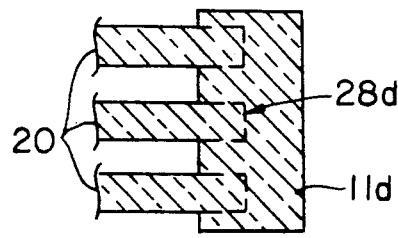
FIG. 10C  FIG. 10D
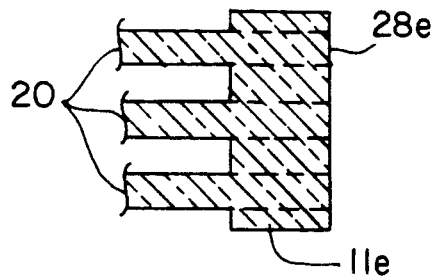
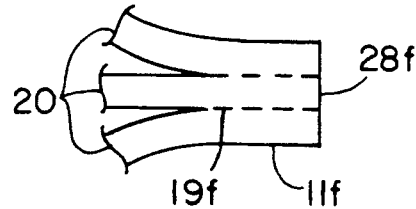
FIG. 10E  FIG. 10F
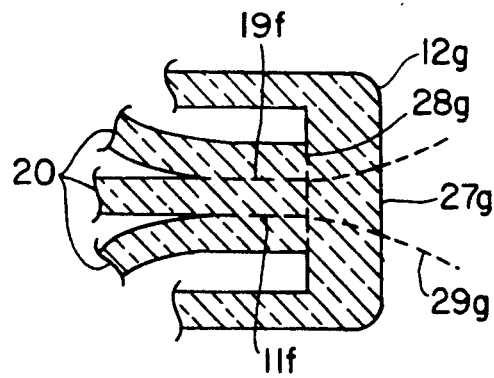
FIG. 10G

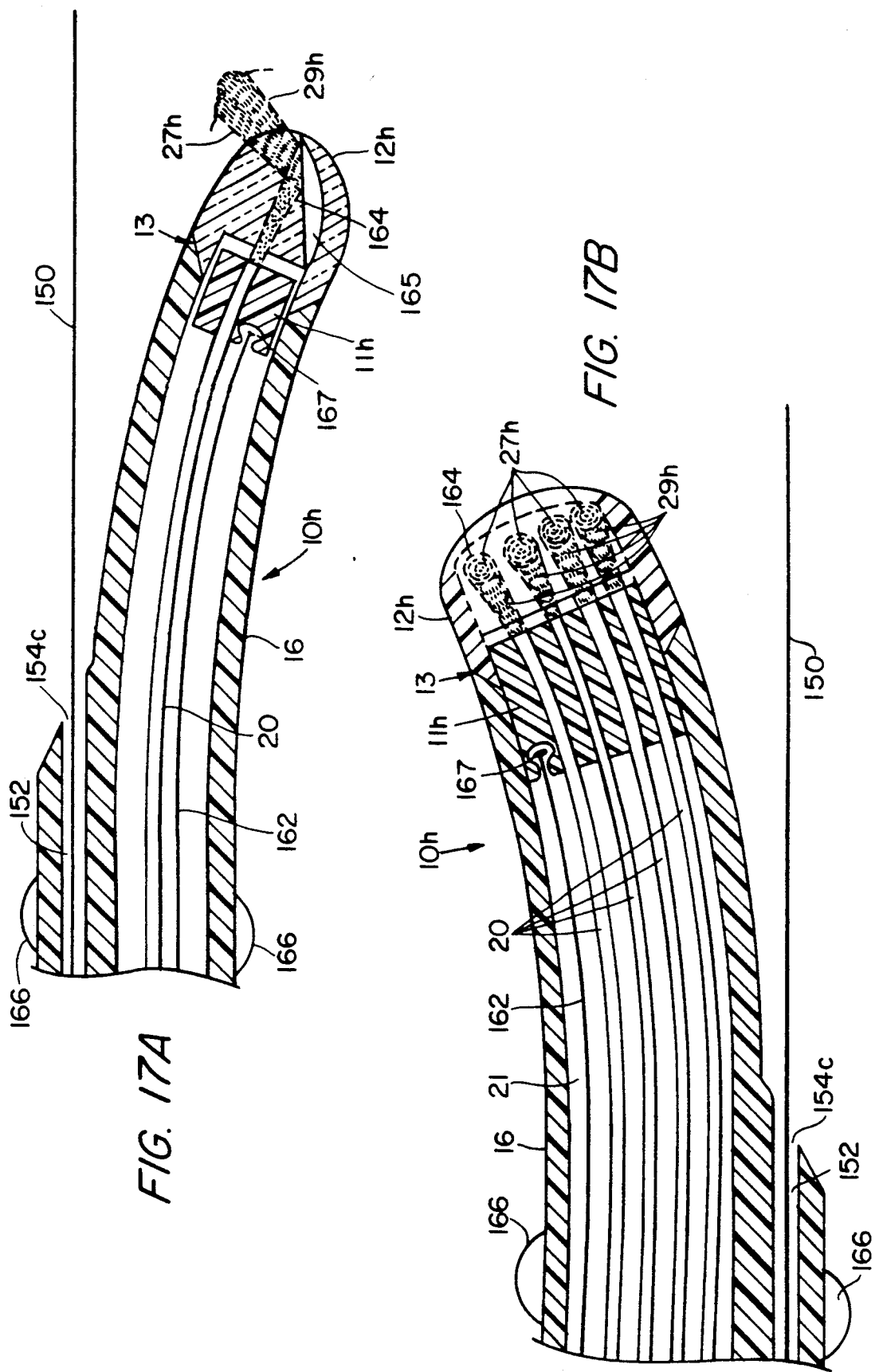

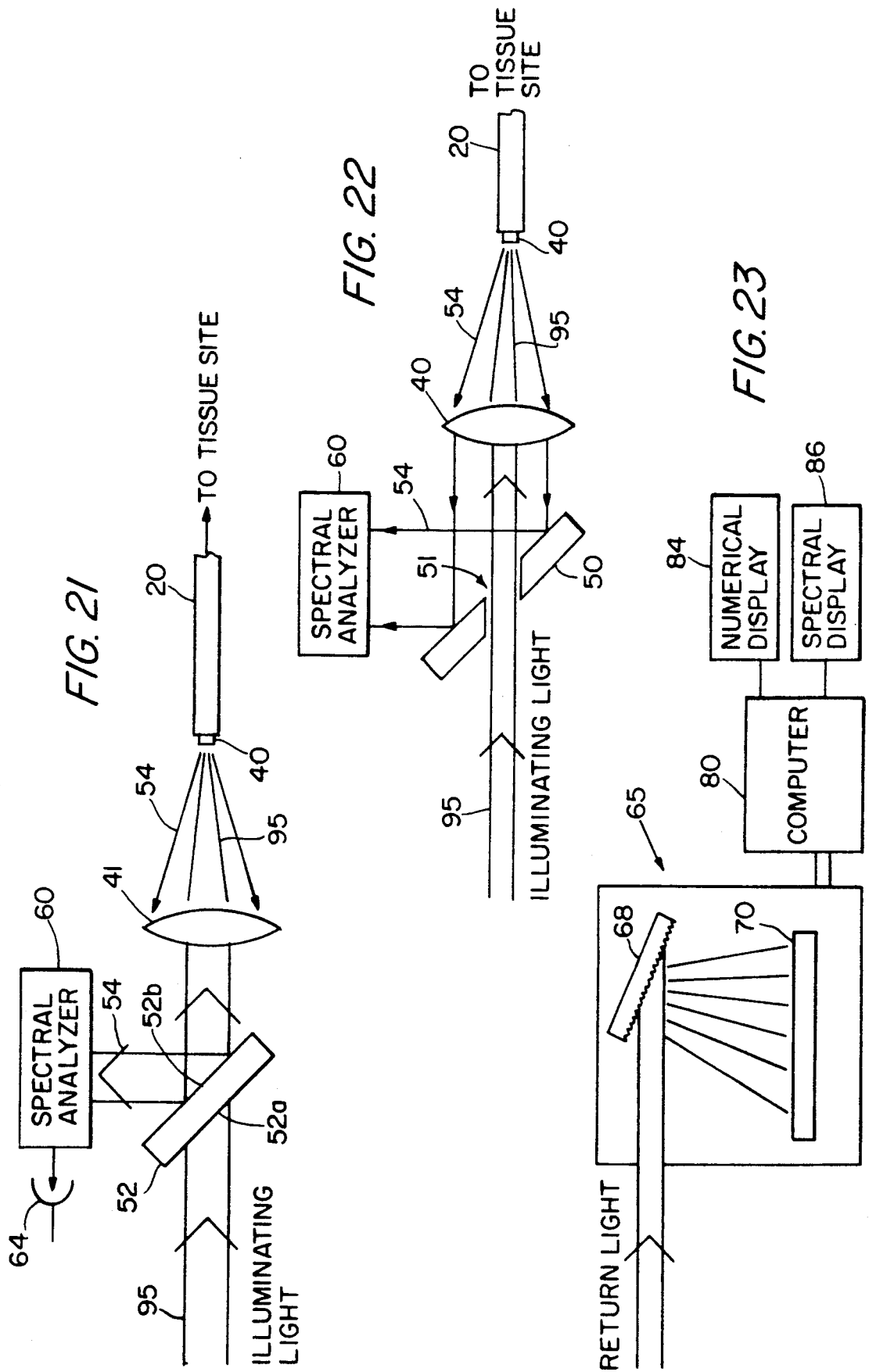

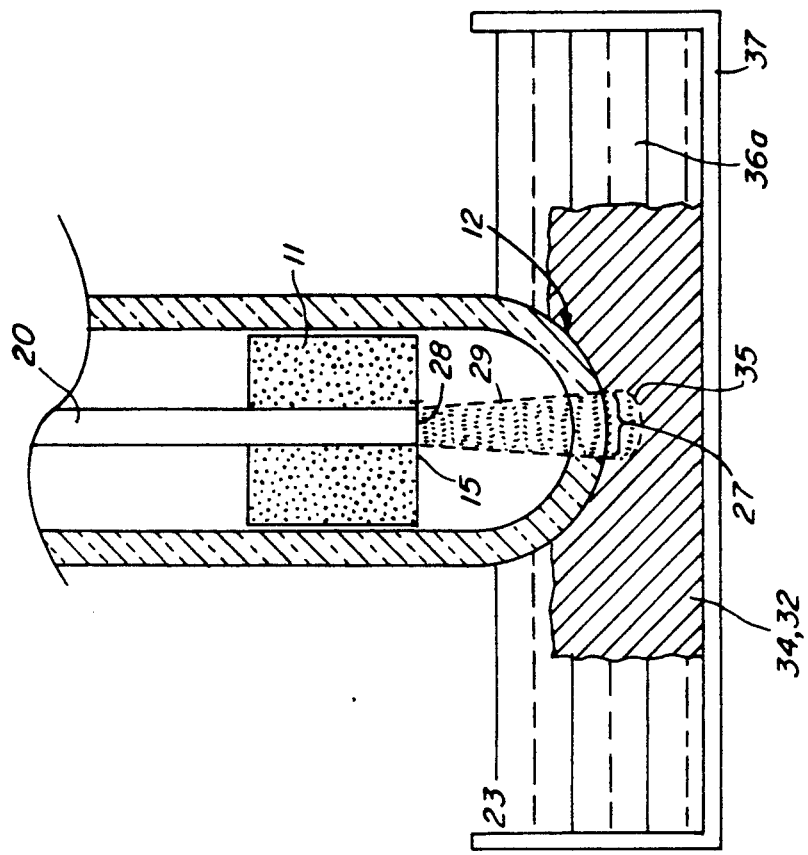
FIG. 27
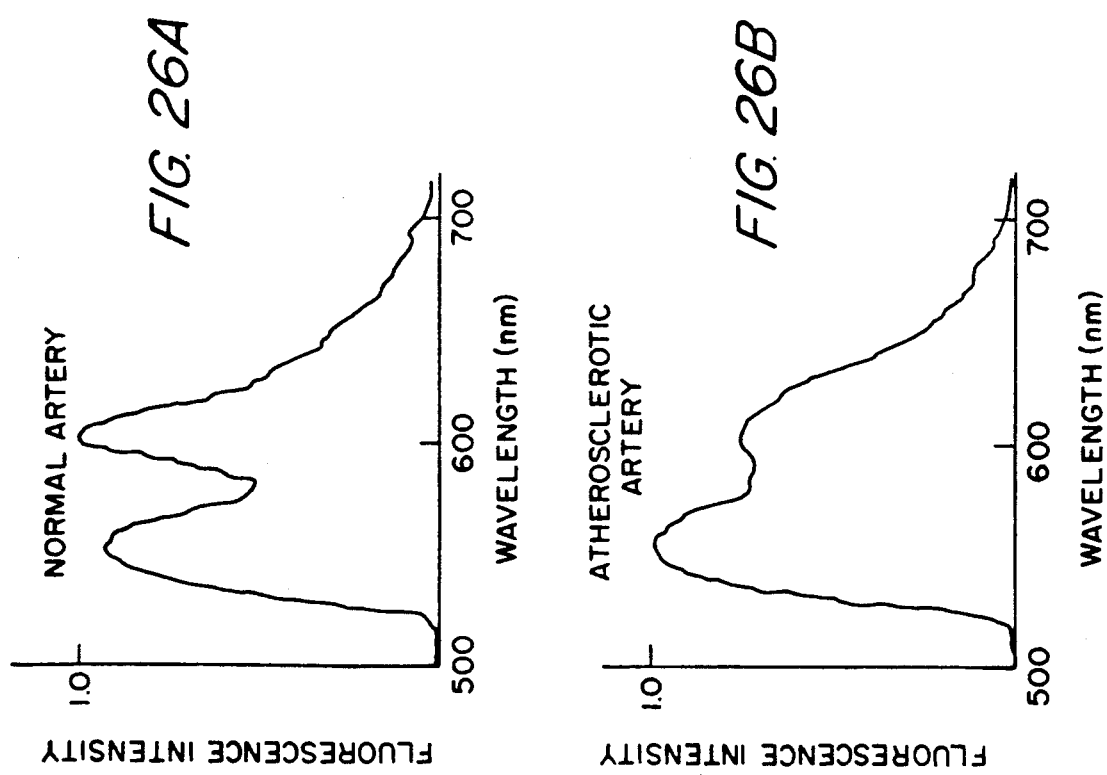
FIG. 26A
FIG. 26B

CATHETER FOR LASER ANGIOSURGERY

RELATED U.S. APPLICATIONS

This is a continuation of U.S. Ser. No. 07/411,326 filed on Sep. 22, 1989, now U.S. Pat. No. 5,034,010 which is a divisional of U.S. Ser. No. 07/058,675 filed on May 26, 1987, now U.S. Pat. No. 4,913,142 which is a continuation of U.S. Ser. No. 06/715,239 filed on Mar. 22, 1985, now abandoned.

I. TECHNICAL FIELD

This invention relates to devices in which optical fibers are provided within a catheter and laser radiation is directed through the fibers for medical applications including diagnosis and removal of arterial or vascular obstructions (angiosurgery).

II. BACKGROUND ART

The term "laser" is an acronym for Light Amplification by Stimulated Emission of Radiation. As used herein, the term is meant to encompass a device which utilizes the principle of amplification of electromagnetic waves by stimulated emission of radiation to produce coherent radiation in the infrared, visible or ultraviolet region. Such radiation has been used in external medical applications, such as for cauterizing, for attaching detached retinas and for removing various skin cancers.

Likewise, optical fibers have been used in a variety of medical applications. An optical fiber is a clad plastic or glass tube wherein the cladding is of a lower index of refraction than the core of the tube. When a plurality of such tubes are combined, a fiber optic bundle is produced. Optical fibers are flexible and are therefore capable of guiding light in a curved path defined by the placement of the fiber.

Fiber optic scopes have been developed for medical technology in order to enable illuminating and viewing access by the medical practitioner to the various interior parts of the body. In many medical applications, fiber optic devices have been combined with laser techniques to properly focus and apply laser radiation to interior parts of the body.

More recently, laser catheters have been constructed in which flexible or rigid hollow tubular devices (catheters) containing optical fibers are inserted into veins or arteries to illuminate internal parts of the body for diagnostic and surgical purposes. Such an application, in which fiber optic bundles are contained within a flexible catheter conduit, is described in U.S. Pat. No. 4,207,874 issued to D. S. J. Choy on Jun. 17, 1980. This fiber optic catheter contains a combination of: (1) a fiber optic viewing bundle; (2) a light source bundle for illuminating the region to be viewed; (3) a laser bundle for delivering laser light to the site for removal of tissue; (4) an annular space around the bundles for fluid supply or suction; and (5) a proximal supply and a transparent reservoir connected to the annular space. All of the above items together constitute a "laser tunneling device". The sole described use for the device is the removal of thrombus in veins for applications in the circulatory system.

The Choy device relies on visualizing the thrombus obstruction in a a vein, via the viewing bundle. It is therefore necessary to purge the blood. As no means of blocking the blood flow is shown in Choy, the Choy device can be used only when the vein is already totally obstructed. As soon as the obstruction is opened even a small amount, blood in the transparent reservoir indicates the end point of the procedure. A partial blockage which causes inadequate flow cannot be visualized or treated by the device. In the case of coronary arteries, an important treatment area for the present invention, complete blockage would cause death of the distal tissue, and so restoring blood flow at such a late state of disease would provide little clinical benefit.

M. Bass, in U.S. Pat. Nos. 3,858,577 and 4,146,019, describes a device which uses a transparent window to protect an optical fiber carrying laser radiation into a body cavity (e.g. the stomach). The window has a possible protective function, that of preventing spattering of debris from the laser tissue interaction back onto the optical fiber in the gas-purged environment. The cleanable or replacable window is in all examples recessed into a metallic or non-optically transparent holder. The design is such as to to avoid contact between tissue and the window. In addition, the cavity formed by the recess would tend to trap fluid, such as blood, absorbing the laser radiation and hindering it from reaching the target tissue.

In Bass, multiple fibers within the catheter body are described, but only for the purpose of replacement in case of fiber failure.

The Bass instrument also includes a flexible fiber optic endoscope for viewing the body cavity as an integral part of the device. Being a visual device, the information which can be provided for diagnosis by the endoscope is limited to what can be seen. In addition, the endoscope is not contained within the windowed enclosure, so the field of view in front of the endoscope must be completely purged of all non-transparent fluids, such as blood or blood substitutes. Such a purge deprives distal tissues of blood and oxygen. Therefore, the Bass instrument is clearly an instrument not intended for use, and cannot be used, in the vascular system.

J. H. Hett in U.S. Pat. No. 4,072,147, describes a device for viewing and for carrying therapeutic laser radiation into a body cavity. This endoscopic device contains a fiber optic bundle image transmitter connected to an eyepiece for viewing; a spotter light path which indicates where the endoscope is aimed; and optical fibers to deliver therapeutic radiation (which need not be visible light) to that visualized spot. This instrument further may contain a protective transparent cover over the distal end of the instrument. It also may incorporate a manually adjustable variable filter in the viewing path so as to protect physicians eye. A servo system connected to the manually adjusted filter can adjust therapeutic laser power.

The Hett instrument is designed only for direct visualization by eye and requires an optical image transmitter coherent fiber bundle. Since it is a visual device, the information about the tissue diagnosis is limited to what can be seen. Also, because visualization is used, the path from the distal end of the instrument to the tissue must be clear, but no means of purging non-transparent fluids (such as blood) is provided. The spotter beam, and hence the therapeutic radiation, is delivered-.to a single location in front on to the side of the distal end of the device: "The image (therapeutic laser beam) is located in a predetermined segment of the field of view . . . ". The device must be physically repositioned each time a different spot of tissue is to be treated. In a blood vessel, treatment of a lesion would be limited to one spot at a time. The difficulty of maneuvering the long flexible catheter to a new spot for each small piece of tissue removed, and the likely damage to the delicate vessel wall from repeated and prolonged manipulation of the device would make its use impractical in such a situation. Finally, since the control of the laser power is connected to the position of the hand operated attenuating filter, such control is essentially manual, and is therefore orders of magnitude slower than an electronic control system. It is inadequate for use in a blood vessel where laser radiation can perforate the wall in less than a second. For all these reasons, the Hett instrument is one which is not intended for an inadequate for, use in the vascular system.

Hussein, et al, in U.S. Pat. No. 4,445,892, describes a vascular fiber-optic catheter with two inflatable balloons which can seal off a segment of a blood vessel, allowing it to be purged. Blood flow is maintained past the distal end. A cylindrical window allows viewing and laser irradiation through the side of the device. The balloons displace the blood and protect the operating portion of the instrument.

A significant lumen in a vessel must already exist to allow insertion of the balloon distal to the lesion, so the instrument could be used as described. In the cases where the lumen is severely stenosed or restricted, or totally occluded, forcable insertion of the distal balloon may fail or cause serious mechanical injury to the diseased vessel. This instrument is least useful in the situation where the need is greatest. Also as the therapeutic laser radiation is angled to the side to avoid hitting the distal balloon, perforation of the artery wall is more likely than if it were aimed forward. Also, the tube holding the distal balloon restricts the field of view. As with Bass and Hett, the device relies on visualization and the diagnostic information is limited as described. Electronic feedback control of the laser power is not included.

The application of laser catheters have been documented in the literature [D. S. J. Choy, S. H. Sterzer, H. Z. Rotterdam, N. Sharrock and I. P. Kaminow, "Transluminal Laser Catheter Angioplasty", Am. J. Cardiol. 50, 1206-08 (1982); D. S. J. Choy, S. H. Stertzer, H. Z. Rotterdam and M. S. Bruno, "Laser Coronary Artery Angioplasty: Experience with Nine Cadaver Hearts", Am. J. Cardiol. 50, 1209-11 (1982); G. S. Abela, S. Normann, D. Cohen, R. L. Feldman, E. A. Geiser and C. R. Conti, "Effects of Carbon Dioxide, Nd-YAG, and Argon Laser Radiation on Coronary Atheromatous Plaques", Am. J. Cardiol. 50, 1199-1205 1982); G. Lee, R. M. Ikeda, R. M. Dyer, H. Hussein, P. Dietrich and D. T. Mason, "Feasibility of Intravascular Laser Irradiation for In Vivo Visualization and Therapy of Cardiocirculatory Diseases", Am. Heart J. 103, 1076-77 (1982); R. Ginsburg, D. S. Kim, D. Guthaner, J. Toth and R. S. Mitchell, "Salvage of an Ischemic Limb by Laser Angioplasty; Description of a New Technique", Clin. Cardiol. 7, 54-58 (1984); and E. Armelin, R. Macruz, M. P. Ribeiro, J. M. G. Brum, M. G. C. Madrigano, P. R. Camargo, J. Mnitentag, P. Pileggi and G. Verginelli, "Application of a Laser Beam in the Vessel Wall Without Interruption of Blood Flow:", Circulation 66 (abstract), II-136 (1982).

In all of these studies the optical fiber conducting the laser light is placed in the artery in an unprotected manner, in direct contact with the blood. Reports in the literature enumerate severe drawbacks in the efficacy and safety of this simple approach. At the tip of the fiber the reaction of the emitted light with the intravascular target is violent. A "crackling" sound during the irradiation process, similar to that of bacon cooking, has been described. The corrosive environment of the blood vessel readily damages the delicate tip of the optical fiber. The light (particularly blue-green argon laser radiation, which is most commonly used) is strongly absorbed by any blood intervening between the tip of the fiber and the tissue target, with the reaction forming debris and gas. There is evidence that red blood cells are damaged, predisposing to the formation of platelet aggregates. In addition to the resultant problem of thrombosis, vascular perforation is a major complication. The latter occurs because of poor control of the laser radiation. Further, even if perforation does not occur acutely, the arterial wall may still be damaged, with the resultant potential for long term aneurysm formation.

Modifications to reduce these complications have been proposed. One approach has been to cover the bare fiber with an absorbing metal tip which is heated by the laser light, forming a hot probe. [T. A. Sanborn, D. P. Faxon, C. C. Haudenschild and T. J. Ryan, "Laser Radiation of Atherosclerotic Lesions: Decreased Incidence of Vessel Perforation with Optic Laser Heated Metallic Tip," J. Am. Coll. Cardiol. (abstract) 3, 490 (1984); G. Lee, R. M. Ikeda, M. C. Chan, J. Dukich, M. H. Lee, J. H. Theis, W. J. Bommer, R. L. Reis, E. Hanna and D. T. Mason, "Dissolution of Human Atherosclerotic Disease by Fiberoptic Laser-Heated Metal Cautery Cap", Am. Heart J. 107, 777-78 (1984)]. This approach is unsatisfactory for several reasons: (i) there is thermal damage to surrounding tissue; (ii) only fatty plaques readily melt away; (iii) the more advanced fiberous and calcified plaques form char and debris; and (iv) the hot tip tends to adhere to the tissue, so when it is removed, the tissue is ruptured.

Despite the scope of the above efforts, a need still exists for accurate control of high power radiation delivered through optical fibers if percutaneous intravascular laser treatment is to reach its full potential.

III. SUMMARY OF DISCLOSURE OF THE INVENTION

In accordance with the invention, an optical fiber, or fibers, which can carry laser radiation is mounted in a flexible inert plastic catheter material with a transparent protective optical shield over the distal end. This assembly constitutes the laser catheter. This catheter is inserted into a blood vessel and the shield, at the distal end, is brought into contact with the plaque. This placement may be facilitated by use of a hollow flexible guide or outer catheter. When the shield is in contact with the plaque or other obstruction site, the intervening arterial blood is pushed away and direct radiation for diagnosis and tissue removal is made possible.

The shield may be in the form of a glass, fused silica, sapphire or other transparent member. The shield may be flat, spherical or lens shaped. The periphery of the shield is bonded to the end of the catheter wall.

The enclosed protected region provided by the shield can be used to mount or incorporate elements of various kinds. Several fibers can be precisely positioned at different locations within the shield. Lenses or mirrors, and mechanical or optical aiming and focusing devices can be mounted inside of the shield. Light can be delivered to the tissue via one fiber, and the reflected light returned by means of the same or another "sensing" fiber for spectroscopic or other forms of analysis. Other detection devices, such as endoscopes, can also be mounted in the shield. The fibers may be secured to each other with an adhesive substance, and likewise may be bonded to the optical shield.

The protective optical shield mechanically displaces the blood and also protects the fiber(s) from the intra-arterial contents. The fiber(s) are anchored so that there is an appropriate distance between the output end of the fiber(s) and the tip of the shield. The catheter and shield are sealed watertight, preventing blood from coming into contact with the internal components. The intervening space may be filled with fluid, or optical surfaces may be optically contacted, or they may be anti-reflection coated to reduce Fresnel reflections and maximize transmitted light.

The optical shield overcomes disadvantages of the bare fibers of the prior art and provides new capabilities. By locally displacing blood, the shield provides a clear field of view between the tip of the fiber(s) and the tissue, without the need for a purge or flush. Visualization via a viewing bundle without flushing also becomes possible. As the blood fluid is an excellent heat sink, this mechanical displacement reduces the highly undesirable transfer of heat from irradiated tissue to the blood.

The shield also provides greater control in delivery of the laser light. The ratio of power to intensity is no longer determined by the core diameter of a fiber. The light emanating from the tip of a fiber is in the form of a cone, the output spot is smallest at the fiber tip and becomes larger with increasing distance from the fiber tip. Therefore, the distance between the end of a fiber and the surface of the shield can be adjusted, for a given application, to optimize the light spot size on the output surface of the optical shield, and therefore on the tissue in contact with it. Spot size can also be varied by means of lenses inserted within the shield, or by mixing the modes of the fibers to varying degrees.

When multiple optical fibers are used, the overall distribution of light from the laser catheter may be controlled by disposing the fibers at different positions and angles. Reducing the light intensity minimizes excessive heating of the tissue due to debris adherent to the tip of the device, a complication which may occur in bare fiber tissue removal. The optical shield also protects the patient in case of fiber failure.

Most importantly, the optical shield of the invention provides a means of delivering a precisely controllable dose of photons to remove a specified volume of tissue. The rate and extent of tissue removal is governed by three independent optical parameters, which can be specified as incident laser power, exposure time, and spot size. Other parameters, which can be derived from these three include the energy delivered (product of laser power and exposure time), incident intensity (ratio of power to spot area), and fluence (product of laser power and exposure time divided by spot area). The ability to remove a specific amount of tissue requires precise control of all three of these parameters.

Spot size cannot be controlled in a bare fiber laser catheter. If the fiber tip is in direct contact with the tissue, the light spot diameter is that of the fiber core (assuming the laser light completely fills the core). With increasing spacing between fiber and target the spot size increases because of the spreading cone of light emanating from the fiber. But, experience shows that even under direct visualization the spacing between the tip of the fiber and the target lesion cannot be accurately controlled. Furthermore, intervening blood and/or debris then limits control of the incident laser power. Hence, controlled tissue removal cannot be achieved in a bare fiber laser catheter. In contrast, experimental evidence presented below will demonstrate that in the laser catheter invention described herein tissue can be removed in a controlled fashion.

The laser catheter can, of course, be used in veins as well as in arteries. It can also be used in other vessels, ducts or body cavities. It can be used to penetrate most types of tissue. In all cases the optical shield of the invention provides the means for controlled delivery of light to the tissue to be treated or removed. The tissue is spectroscopically identified and the tissue is removed as needed. Such removal enlarges an existing lumen or creates a channel wherein solid tissue is present. The laser catheter is advanced into the new channel and the process is repeated. Mechanical control devices built into the laser catheter body can be used to bend or position the laser catheter and so enlarge the channel internally, without necessarily enlarging the opening through which it was introduced. Thus, lesions larger than the laser catheter and those with irregular shapes may be removed from any tissue within the body.

IV. BRIEF DESCRIPTION OF THE DRAWINGS

FIG. 1 is a broken longitudinal sectional view of a laser catheter showing the preferred embodiment of the invention.

FIG. 1A is a cross-sectional view of the distal end of the laser catheter of FIG. 1 taken along line I—I.

FIGS. 7A-F show alternate embodiments of the optical shield of the laser catheter.

FIGS. 8A-E is a process diagram showing a method of fabricating an optical shield in accordance with the invention.

FIGS. 9A-D is a cross-sectional view of alternate embodiments of the optical shield.

FIGS. 10A-G show various embodiments of optical fiber plugs for the laser catheter.

Figure 11A:
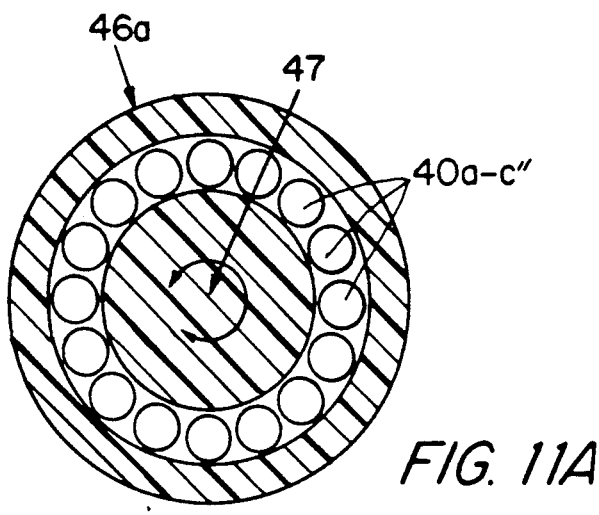
Figure 11B:
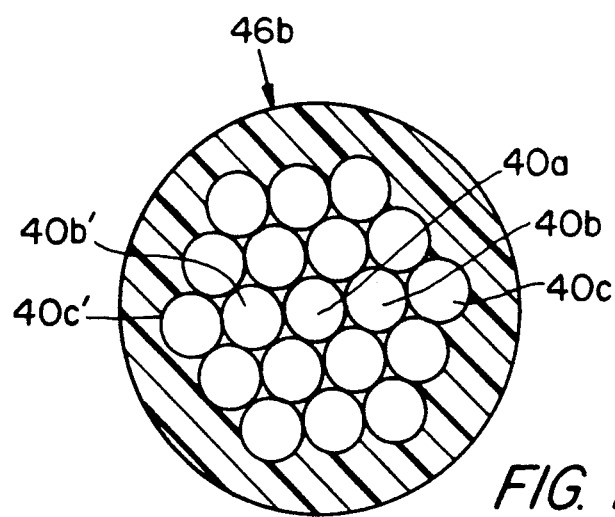

FIGS. 11A-B show alternate embodiments of the optical fiber array of the proximal end of the laser catheter.

Figure 12A:
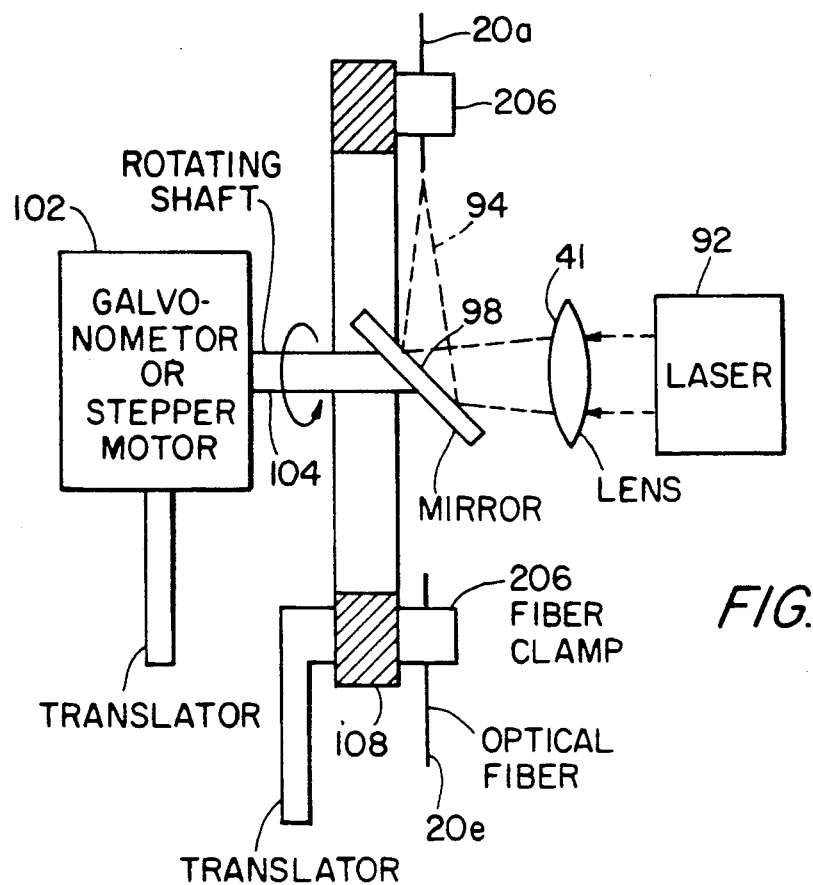
Figure 12B:
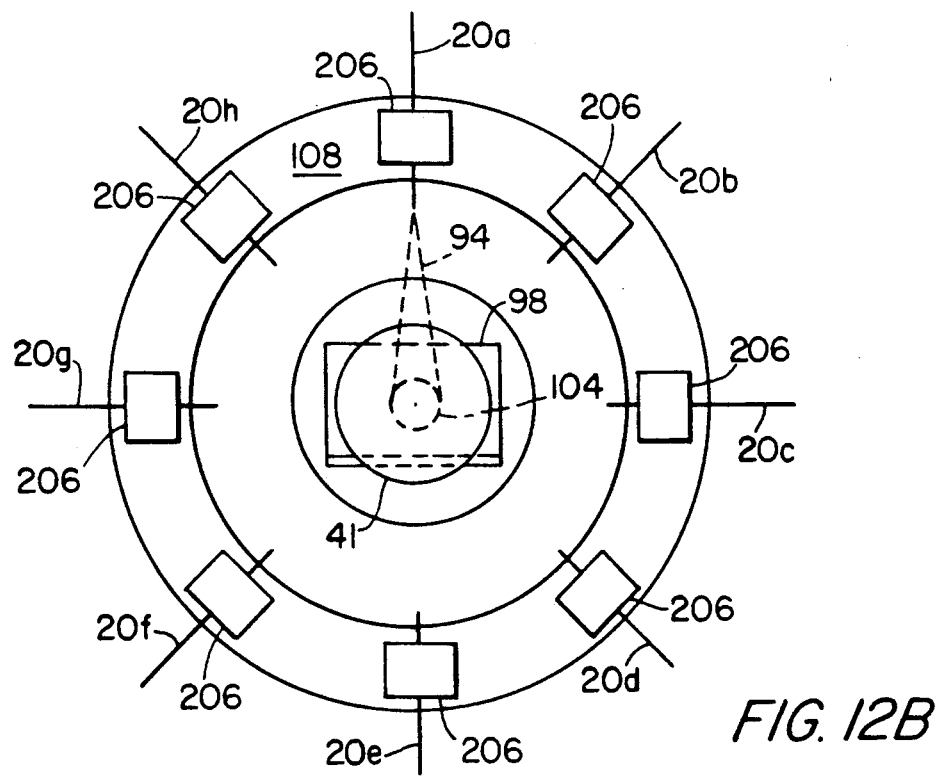

FIGS. 12A and 12B are side and top views, respectively, of another alternate embodiment of the optical fiber array of the proximal end of the laser catheter, and the associated rotating mirror fiber selector system.

FIGS. 13 A-F show optical shield embodiments with various types of optical elements incorporated. FIG. 13A: lens; FIG. 13B: mirror; FIG. 13C: holographic element; FIG. 13D: prism; and FIG. 13E: multiple lenses; FIG. 13F: acousto-optic deflector.

FIGS. 13 G-J show methods of deflecting the optical fibers in the optical shield of a laser catheter. FIG. 13G:

electromechanical device; FIG. 13H: control wires; FIG. 13I: balloons; FIG. 13J: angled fibers.

Figure 14:
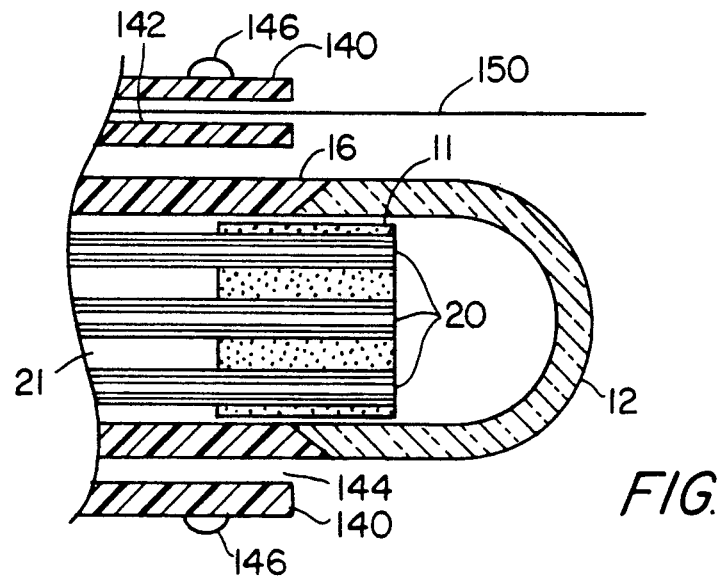

FIG. 14 is a sectional view of the distal end of a laser catheter disposed within a guide catheter.

Figure 15:
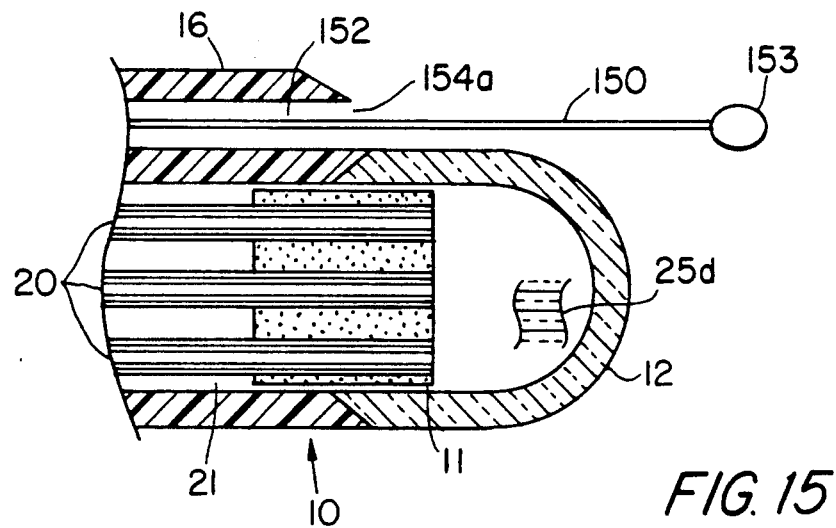

FIG. 15 is a sectional view of the distal end of a laser catheter which incorporates a guide wire in a side lumen.

Figure 16:
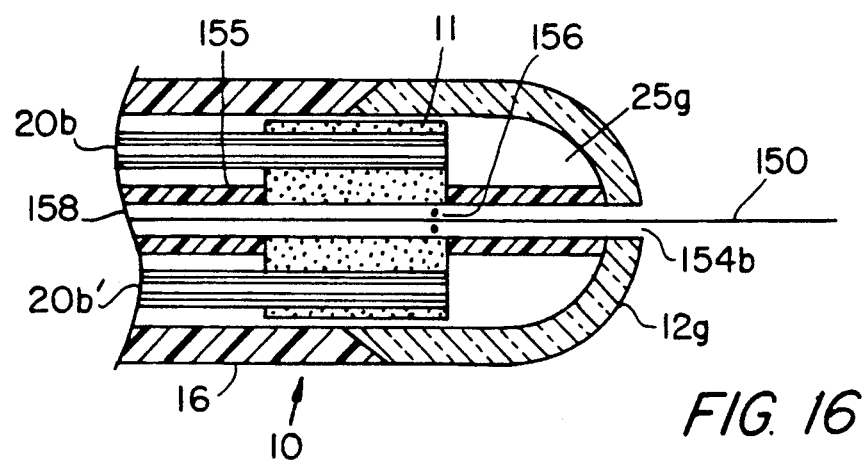

FIG. 16 is a sectional view of the distal end of a laser catheter which incorporates a guide wire in a central lumen.

FIGS. 17A-D show several views of the distal end of a laser catheter which incorporates a guide wire and a deflecting wire.

Figure 18:
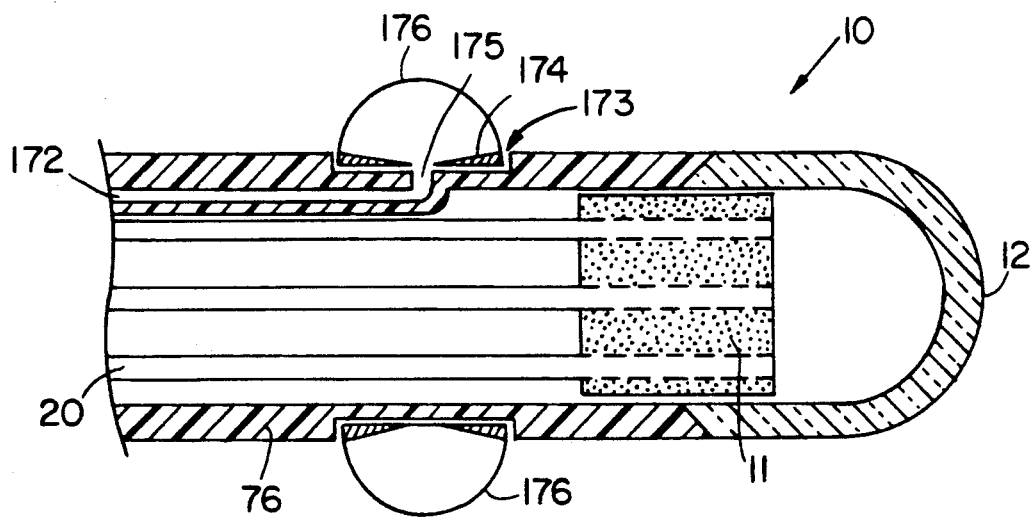

FIG. 18 is a sectional view of the distal end of a laser catheter which incorporates a balloon on a rotary joint.

Figures 19, 20:
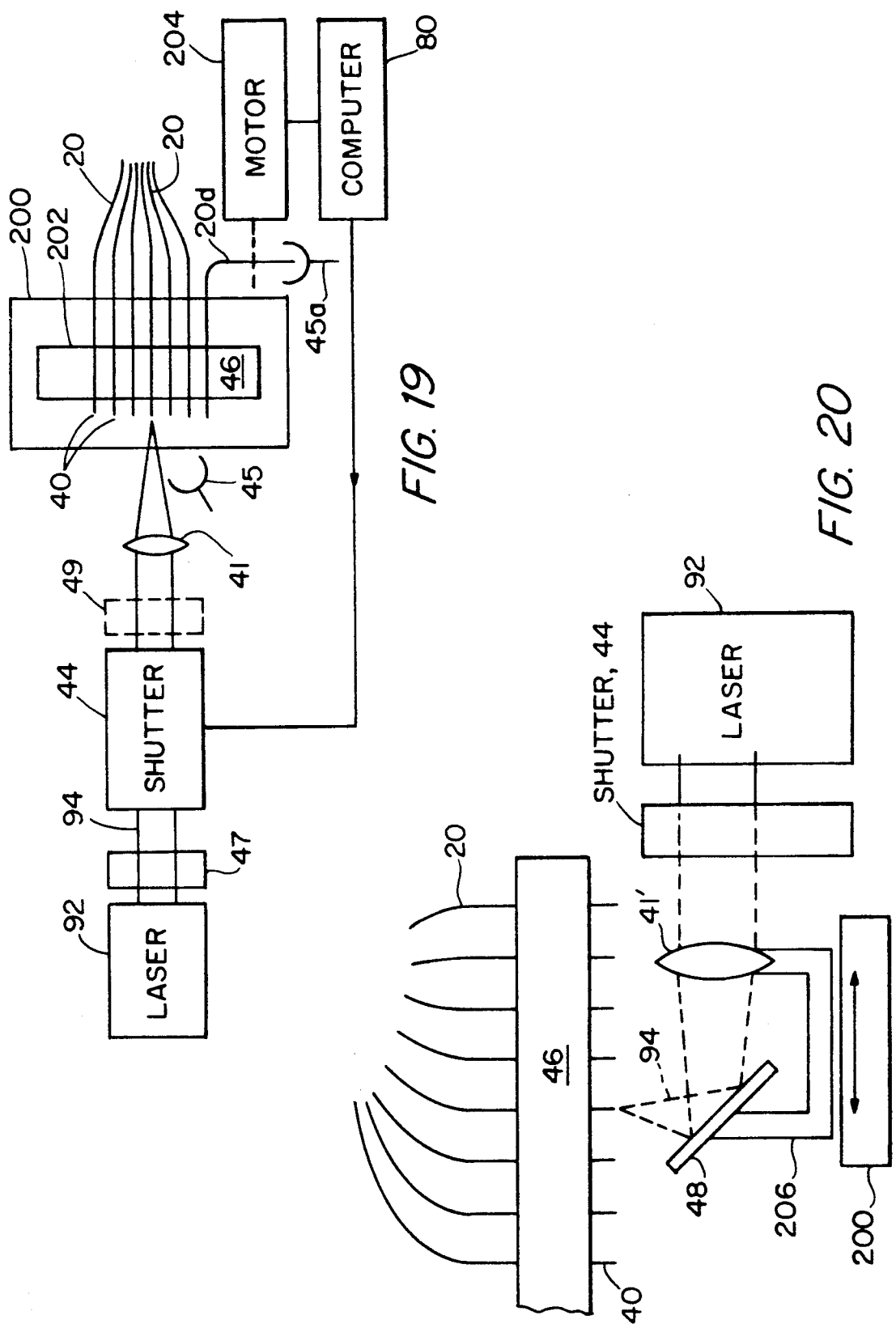

FIG. 19 is a block diagram of a linear array fiber selector system in accordance with the invention.

FIG. 20 is an alternate embodiment of a linear array fiber selector system in accordance with the invention.

FIG. 21 is a schematic diagram of a method and apparatus wherein the same optical fiber may be used for illuminating and collecting return light for spectral analysis.

FIG. 22 is an alternate embodiment of the apparatus of FIG. 21.

FIG. 23 is a schematic of a multichannel spectral detector which may be used in connection with the system of the present invention.

Figure 24:
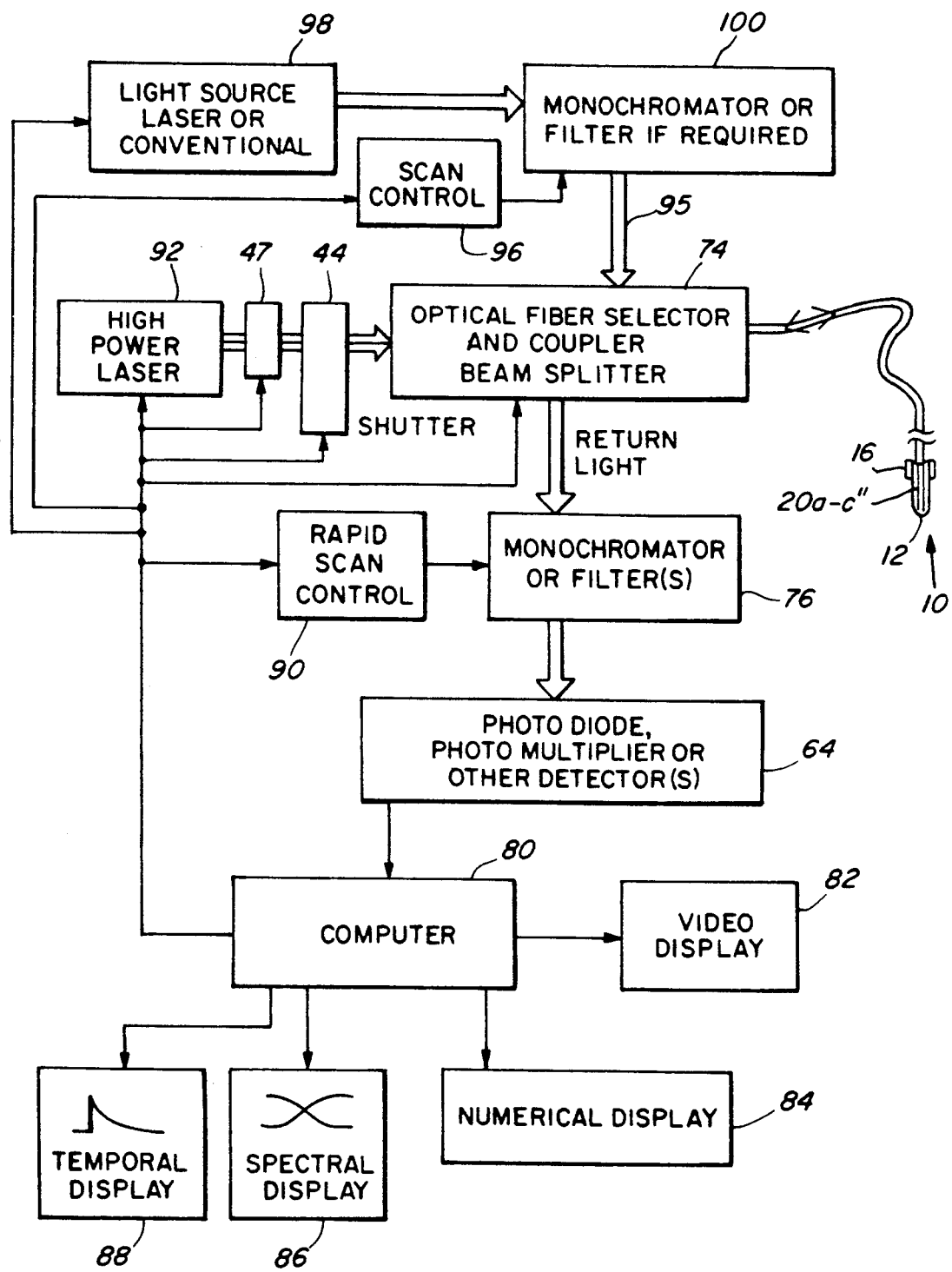

FIG. 24 is a block diagram of a typical system in accordance with the invention for removal of plaque in an artery.

Figure 25:
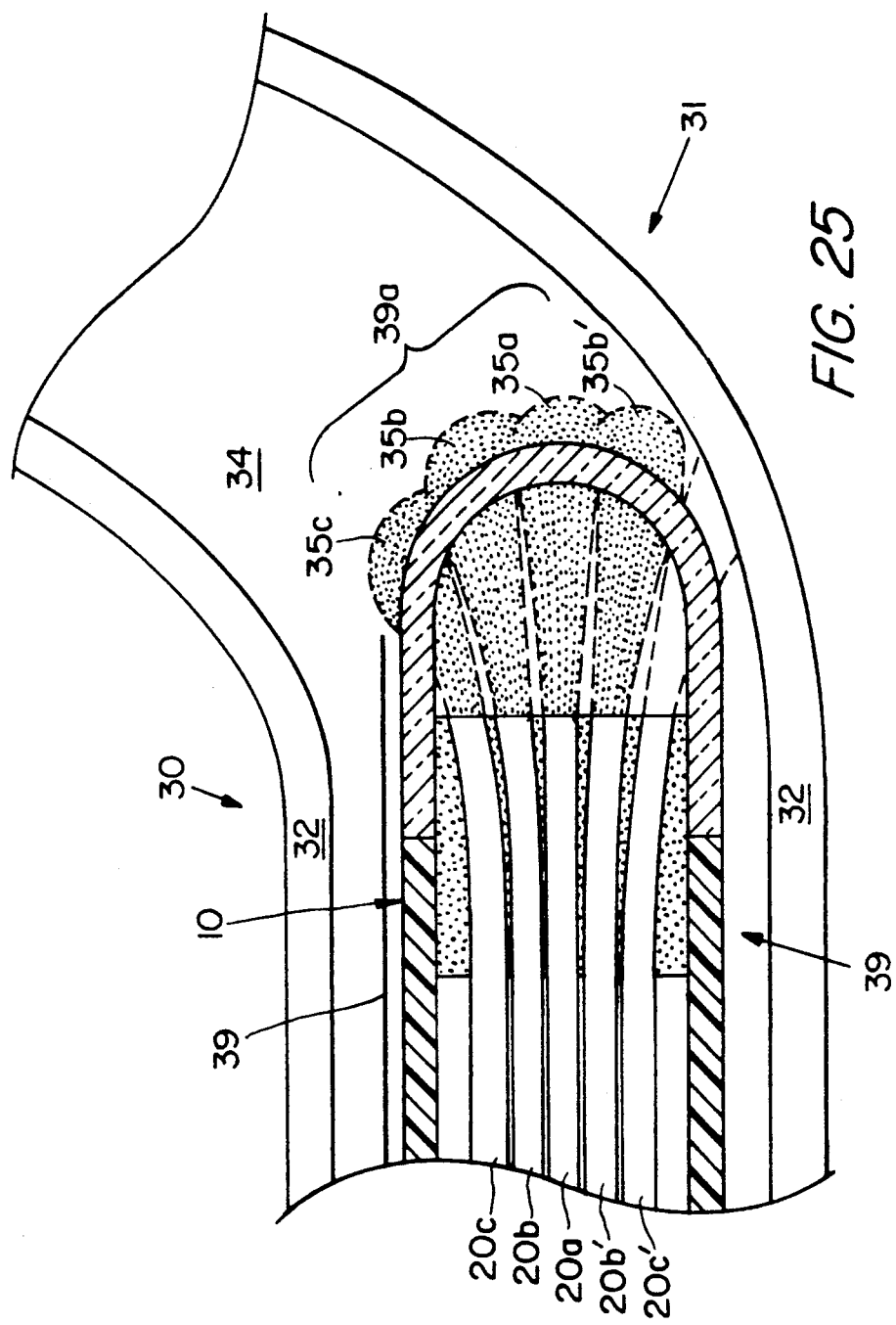

FIG. 25 is a sectional view of a laser catheter embodiment disposed in the bend of an artery, showing the device in operation.

FIGS. 26A and 26B show data of fluorescence intensity versus wavelength taken for normal artery 27A and plaqued artery 27B, respectively.

Figure 28A:
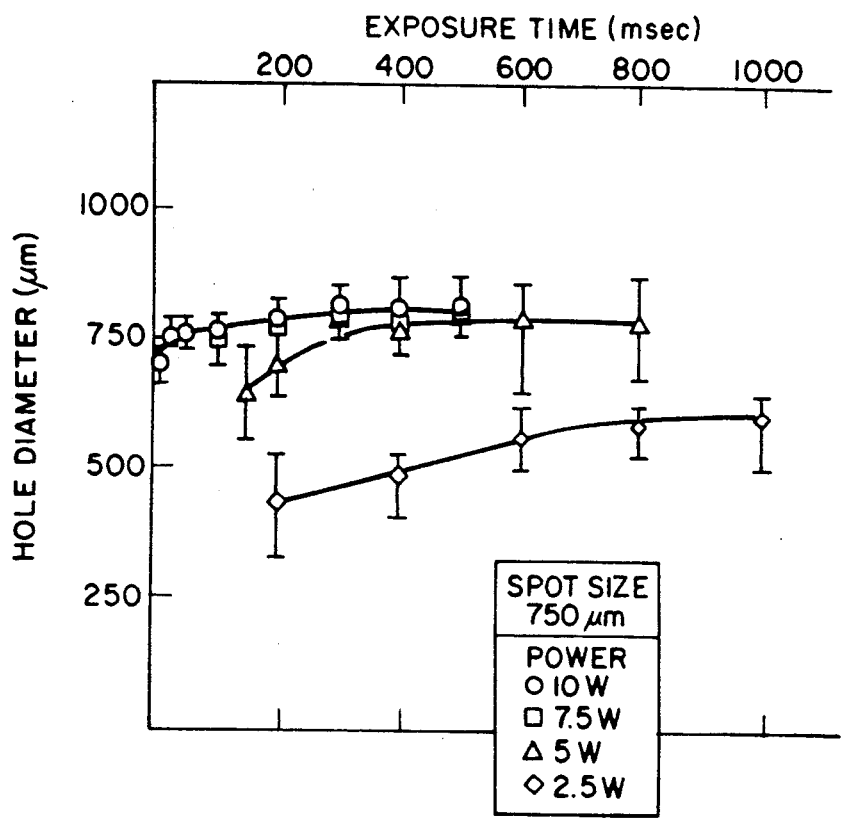
Figure 28B:
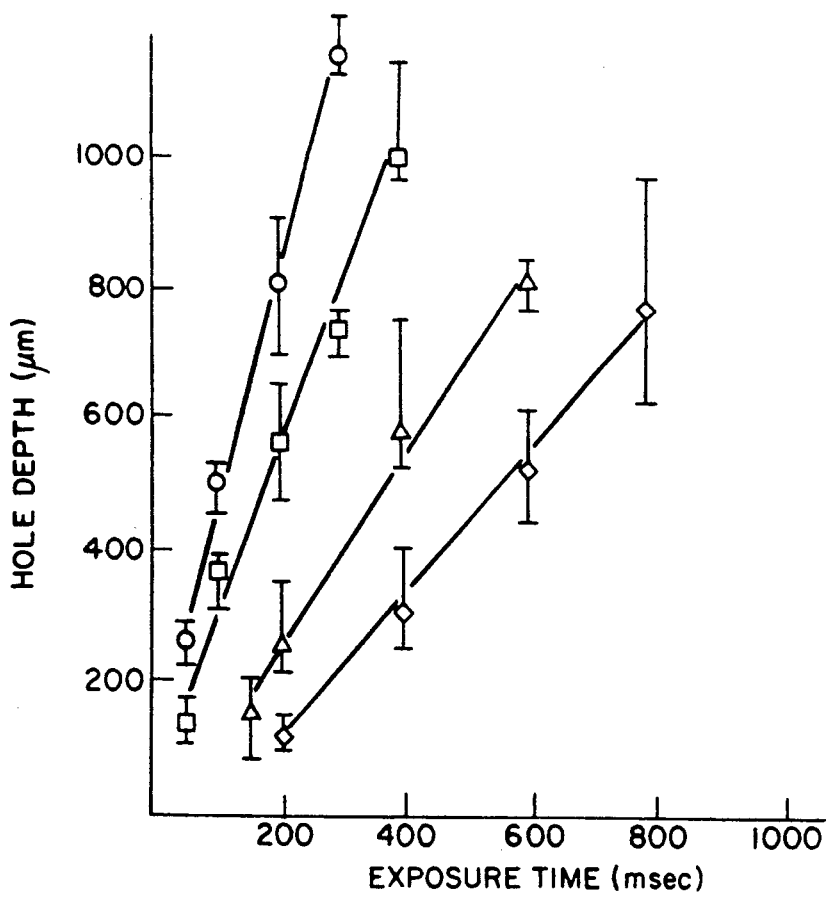

FIG. 27 shows the experimental arrangement for which the data of FIGS. 28A and 28B were taken.

FIGS. 28A and 28B are plots of depth and diameter, respectively, of holes formed by laser ablation in samples of atherosclerotic plaque with a 750 um spot size at various powers.

V. BEST MODE OF CARRYING OUT THE INVENTION

V.A. Components

V.A.1. Laser Catheter, Preferred Embodiment

FIG. 1 shows the preferred embodiment of the entire laser catheter 10 in broken longitudinal section. It is terminated at the distal end by the optical shield 12 and at the proximal end by the fiber optic coupler 46. The flexible catheter body 16, with lumen 21, is typically ½ to 2 meters long and is designed for insertion into or in contact with the patient. A protective enclosure 18 which connects the catheter body 16 to the coupler 46 is preferably short but may be of any length. The optical shield 12 is a transparent enclosure made of fused silica, glass, or sapphire or other optically transparent material capable of withstanding heat, steam and high laser power. Optical transparency may include ultraviolet, visible and infrared light, depending on the light and laser sources used.

The distal end of optical shield 12 of FIG. 1 is shown with a hemispherical cross section, but it may also be rectangular, flat, lens-shaped or of any other shape. The optical shield 12 may be secured to catheter body 16 by a butt joint 13a, as in FIG. 1, or by a tapered joint 13, as in FIG. 2. The joint may be overlapping if desired. A bonding agent or wrapping material may be used to secure the joints 13 or 13a.

Optical fibers 20a,b,b',c,c' are disposed within the catheter body 16 and have a distal termination in the vicinity of the optical shield 12. The corresponding proximal ends 40a,b,b',c,c' of optical fibers 20a,b,b',c,c' are secured by the fiber optic coupler 46. The distal ends of the optical fibers 20a-c' are secured in the material of plug 11. The optical fibers 20a-c' may be angled with respect to the axis of symmetry, as shown in FIG. 1, or they may be straight and coaxial with the distal end of the laser catheter 10, as shown in the longitudinal section FIG. 2.

The preferred embodiment of the laser catheter 10, shown in section in FIG. 1 and in cross section in the plug at the distal end in FIG. 1A, contains a set of nineteen optical fibers, consisting of a central optical fiber 20a, a first ring of six optical fibers represented by 20b,b', and a second ring of twelve optical fibers 20c,c'. An alternate embodiment, the distal end of which is shown in the longitudinal section of FIG. 2 and the cross section of FIG. 3, contains seven optical fibers, including a central optical fiber 20a and a first ring of six optical fibers 20b,b'. In either case each optical fiber is composed of a core 22, a cladding 24 with lower index material than the core 22, and a protective buffer 26 which may or may not extend to the distal end of the fiber. In the preferred embodiment the core 22 and cladding 24 are fused silica or glass or fluorite glass, so as to withstand high laser power.

The preferred embodiment of the fiber optic coupler 46, at the proximal end of the laser catheter 10, is a flat linear array of the optical fiber ends 40a-c' of optical fibers 20a-c'. In addition, optical fiber ends 40b" and 40c" depict optical fibers which do not appear in the sectional drawing FIG. 1 of the distal end of the laser catheter. The coupler 46 holds all nineteen optical fibers 40a-c" in a linear array. An additional optical fiber, shown as 20d in FIG. 19, may be incorporated if desired, with one end disposed in the proximal linear array and the other end connected to a laser power monitor. Other geometries for the coupler 46 may also be used.

Figure 2:
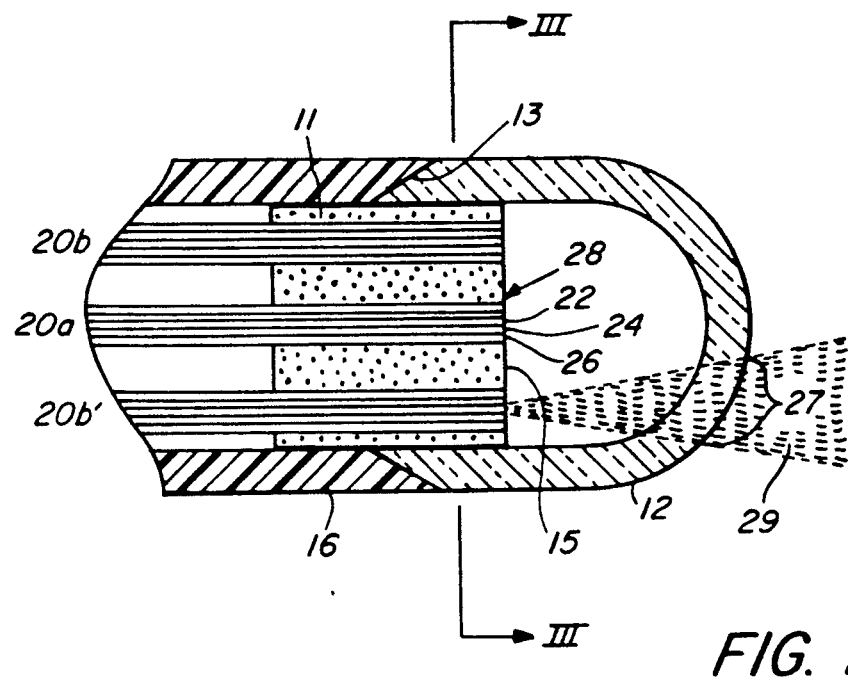
FIG. 2 is a longitudinal section of the distal end of a seven fiber laser catheter.
Figure 3:
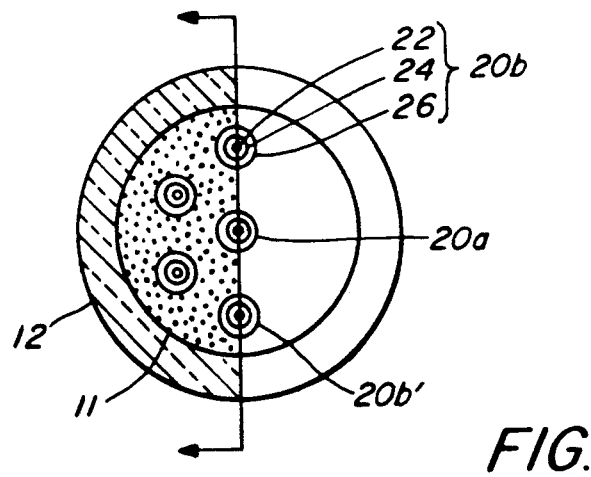
FIG. 3 is a cross-sectional view of the distal end of the laser catheter of FIG. 2 taken along line III—III.

The distal end of each of the optical fibers 20a-c' is terminated in a surface with an optical finish 28 on the core and cladding. This surface may be flush with or protrude from the securing plug 11. In the preferred embodiment the distal ends of the optical fibers 20a-c' are secured by a plug 11 formed of epoxy which is molded around the optical fibers 20a-c'. The molded epoxy plug 11 has an optically ground and polished surface 15, as shown in FIGS. 1 and 2. This plug 11 may be secured to the optical shield 12, to the catheter body 16, or preferably to both. Epoxy plug 11 adds strength to the optical shield 12 and to the joint 13a or 13 with the catheter body 16. As shown in FIG. 1, the optically polished distal ends 23 of optical fibers 20a-c' provide an exit surface for the laser beam or diagnostic light beam 29. FIG. 1 shows a conical beam of laser light 29 exiting optical fiber 20, forming spot 27 on the outer surface of optical shield 12. Addition of an anti-reflection coating 25b to this optically polished surface 23, and to one or both surfaces 25a,c of the optical shield 12, will reduce Fresnel reflections of the beam 29. Fresnel reflections reduce delivered laser power, and the reflected beams may damage the plug or irradiate tissue in an unintended location.

The optical fibers 20a-c' must be able to accept laser radiation at their proximal ends 40a-c', FIG. 1. In the embodiment of FIG. 1 the proximal ends of all the optical fibers are arranged in a linear array and epoxied between a pair of glass slides to form the proximal input end array 46. This assembly is ground and optically polished as a unit. An additional optical fiber 20d of FIG. 19 going to a power monitor may also be included. Linear translation of this array 46 past the laser beam or, conversely, translation of the incident laser beam past the array 46 will allow selection of the optical fiber 20a-c' to be activated.

The laser catheter 10 permits delivery of high power laser radiation from the coupler 46 at the proximal end through the optical fibers 20a-c' and through the optical shield 12 to the tissue to be treated. The laser catheter 10 may also be employed to deliver spectral diagnostic radiation, either from a laser or a conventional light source. The scattered or fluorescent light returning from the tissue passes through the optical shield 12 and re-enters the distal ends of the optical fibers 20a-c', and exits the proximal ends of the optical fibers 40a-c' in the coupler 46, where it may be analyzed. Returning scattered light or fluorescence can also be collected and analyzed during high power treatment irradiation, and can provide a signal for feedback control.

Radio-opaque material may be incorporated in the laser catheter 10 to aid visualization by fluoroscopy. There are several locations at which such material can be added, such as: incorporation in the catheter body 16 material, in the buffer 26 of the optical fiber 20, in the molded plug 11 material, or within the silica or glass of the optical shield 12. A metal band or wire 13f,g,h, shown in FIGS. 7A-D, may be placed around the laser catheter 10 near the distal end, which can serve both as a radio-opaque marker and provide mechanical support to the optical shield 12. A combination of these radio-opaque indicators may be best for optimum fluoroscopic observation of the laser catheter 10 when it is used percutaneously.

Figure 4:
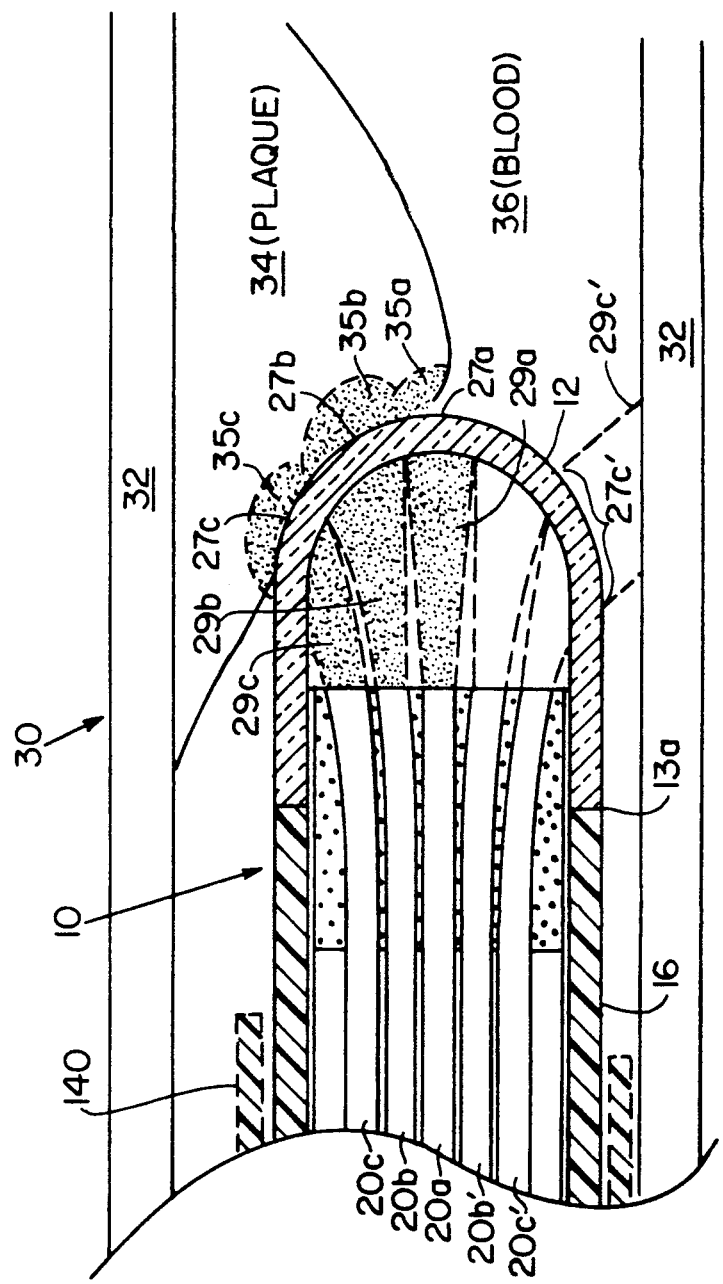
FIG. 4 is a sectional view of a laser catheter embodiment with multiple optical fibers disposed in an artery 30, showing the device in a typical operating environment.

FIG. 4 shows the laser catheter 10 in a typical application, to remove plaque 34 from artery 30 which is partially obstructing the lumen formed by artery wall 32. In the embodiment of FIG. 4 the optical fibers 20a-c' are arrayed such that each of the laser spots 27a-c' on the exterior surface of the optical shield 12 formed by exiting laser beams 29a-c' slightly overlap with adjacent spots. Assuming the diameter of the hole or nibble produced in the irradiated tissue to be the same as the spot size of the impinging radiation, this overlap condition insures that any and all plaque 34 in contact with the distal end of the optical shield 12 can be irradiated and removed by selecting the correct optical fiber(s) 20a-c'. The overlap of spots 27a-c' insures that laser radiation can be delivered through all of the surface of the distal end of the optical shield 12.

The above description assumes that the diameter of the hole or nibble produced in the irradiated tissue is the same as that of the spot of impinging radiation. This is true when the fluence of the impinging radiation is sufficiently high; otherwise the hole diameter will be somewhat smaller than that of the incident spot. In this case, in order to insure that all plaque in contact with the distal end of optical shield 12 can be removed, the optical fibers 20a-c' in the plug must be arrayed so that the degree of overlap of the laser spots on the exterior surface of the optical shield is accordingly greater. Experimental information describing the relationship between spot size and hole diameter is presented in Sec. V.B.2 herein.

Referring again to the application example of FIG. 4, the optical shield 12 of the laser catheter 10 is brought in contact with tissue such as plaque to be removed. Laser light is applied through "fired" optical fiber 20a, as indicated by the shaded area, removing a "nibble" 35a of plaque 34. Optical fibers 20a,b,c are fired sequentially, removing overlapping "nibbles" 35a,b,c. Additional fibers, not illustrated in the section drawing, aimed at plaque are also fired. Optical fibers 20b' aimed at blood 36, and 20c' aimed at artery wall 32, are not fired. Removal of plaque nibbles 35a,b,c allows the laser catheter 10 to be advanced.

V.A.2 Optical Fiber Mode Mixer

Figure 5:
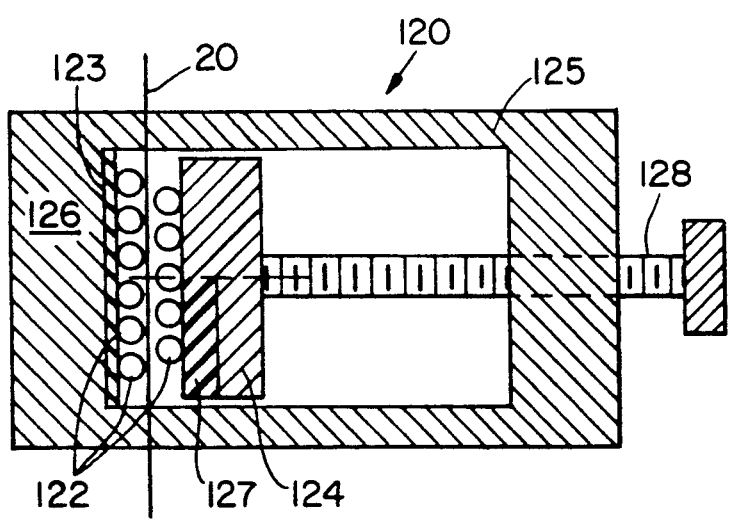
FIG. 5 is a sectional view of a mode mixer used in conjunction with the laser catheter invention.
Figure 6:
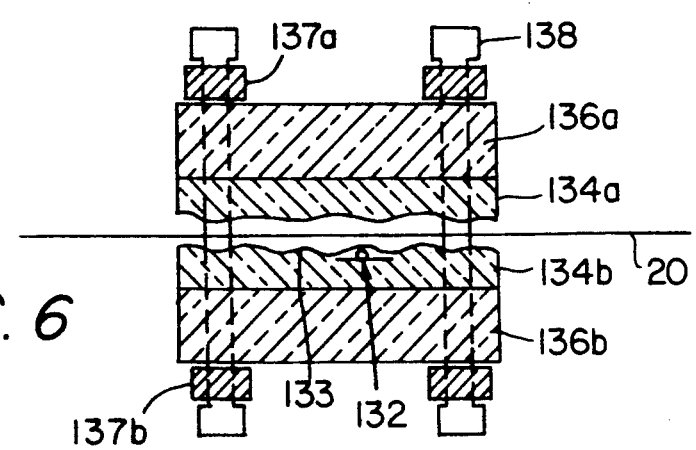
FIG. 6 is a cross-sectional view of an different embodiment of a mode mixer.

In the preferred embodiment an adjustable mode mixer is used to mix the modes in the optical fibers 20a-c' and increase the angular divergence of the exiting laser beams. The preferred embodiment of the mode mixer 120 is shown in FIG. 5; an alternate embodiment is shown in FIG. 6.

Since the diameter or "size" of each spot 27a-c', FIG. 4, on the distal surface of the optical shield 12 is dependent on the divergence angle of the respective exiting laser beams 29a-c', this spot size may be adjusted and overlap of adjacent spots optimized by mixing the modes of the optical fibers 20a-c'. Microbends, which mix the modes, are made by placing the optical fibers against small rod-shaped structures 122 with bending surfaces, such as wires or a nylon monofilament molded projection or the like, and applying pressure by means of a movable pad 124.

Two or more bending surfaces 122 can be placed in series by mounting the wires 122 on a support block 126. The material of pad 124 at the surface at which pressure is to be applied to the fiber(s) should be chosen to be somewhat compliant, such as rubber. Rod-shaped structures with bending surfaces 122 may be affixed to this surface. One or more screws 128 press pad 124 against the rod-shaped structures 122 with the optical fiber(s) 20 in between. The support block 126 may be made of transparent materials so as to view the optical fibers 20a-c' as they are mixed. Excessive pressure will cause excess light to be scattered from the microbends in the optical fibers 20a-c', and this can be observed through the transparent block 126.

One or more mode mixers 120 may be placed in permanant positions on optical fibers 20a-c' of the laser catheter 10 near the proximal end. In this case a removable pressure pad 124 presses the optical fibers 20a-c' against a removable wire support or molded microbend surface 123, and the assembly is potted in epoxy and removed from the frame 125.

V.A.3. Laser Catheter, Alternate Embodiments

Various alternate embodiments of the laser catheter 10 are possible. Beginning with the distal end of the device, and referring to FIG. 7A-F, the optical shield may have a square internal and external surface shape 12a, a slightly rounded external one 12b, or a combination of flat internal and round external surface shape 12c. An asymmetrical shape 12d, as well as fully rounded shape 12 of FIG. 1, may be used if the device is to be moved sideways or at an angle to the forward direction.

Figure 7A:
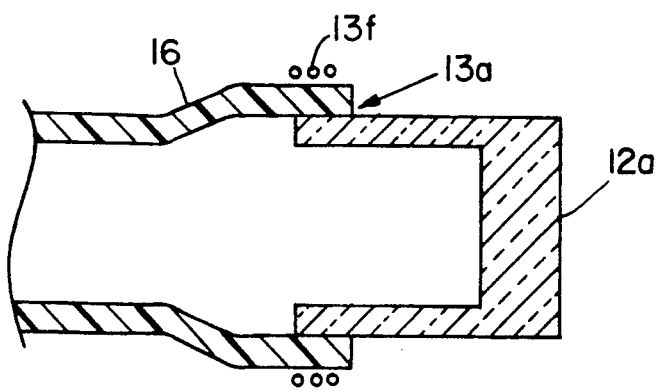
Figure 7B:
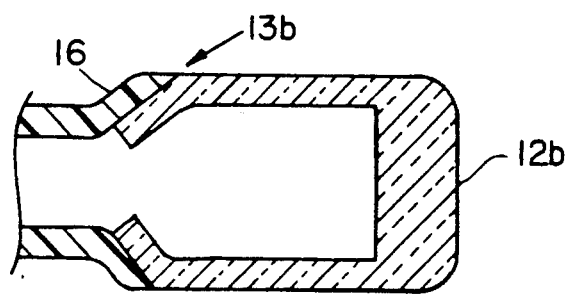
Figure 7C:
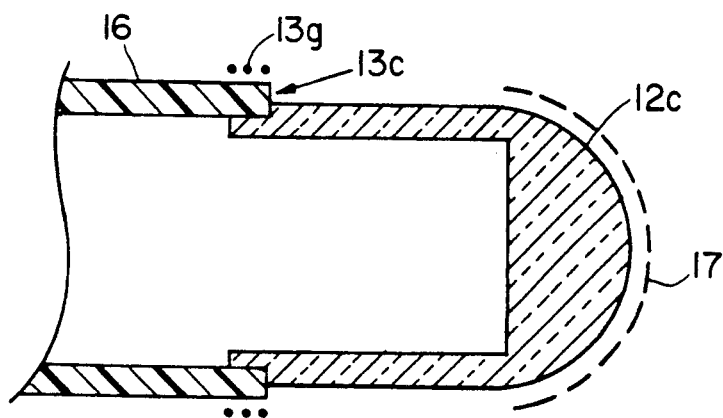
Figure 7D:
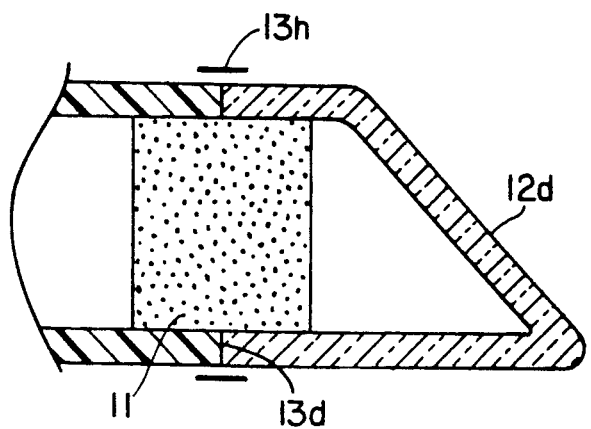
Figure 7E:
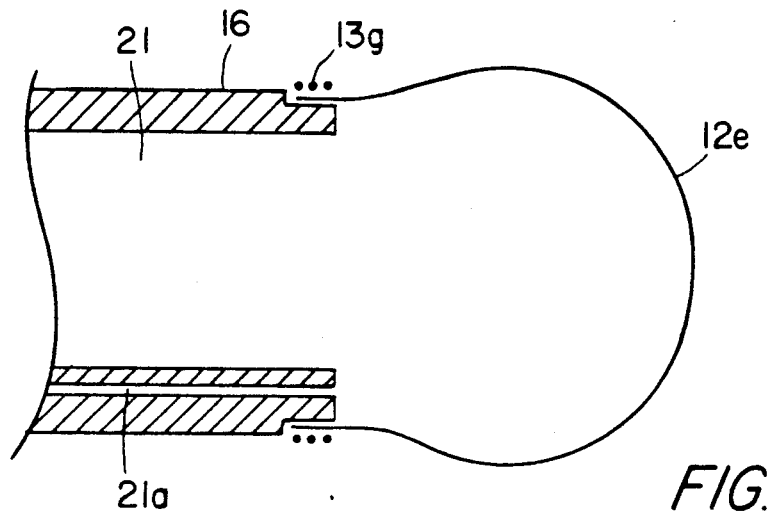
Figure 7F:
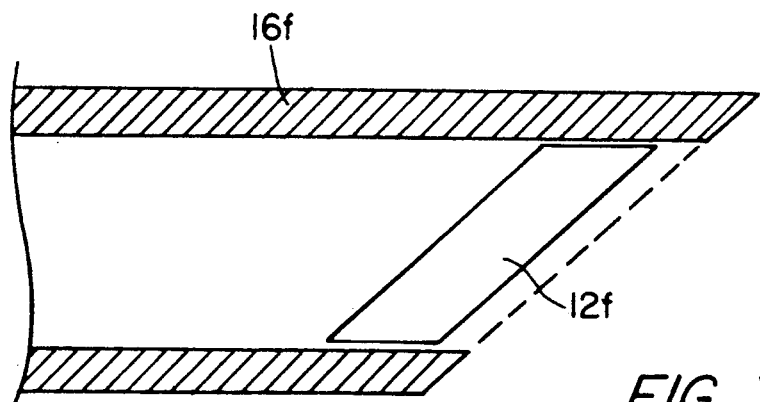

A flexible balloon 12e may also be used as an optical shield as shown in FIG. 7E. Pressurizing gas or fluid to inflate the balloon optical shield 12e may be supplied from the central lumen 21 of the laser catheter body 16, or from an auxillary lumen 212. The geometry of this optical shield can be adjustable, and may partially conform to the tissue it contacts. A deflated balloon 12e will be more readily inserted and removed, and the expanded balloon 12e may displace blood over an area larger than the catheter body 16 diameter. The balloon optical shield 12e may be made of translucent rubber or soft plastic. The use of silicone rubber or fluorocarbon polymers is suggested be to withstand high laser power and heat. A rigid metal tube or cannula 16f may be used with an optical shield that is a transparent disc 12f. The cannula 162 may be cut at an angle 16b so as to aid in insertion into tissue. The optical shield 12f may be angled as shown or at right angles to the cannula.

There are also a variety of embodiments for the joint 13 between the optical shield 12 and the catheter body 16. FIGS. 7A-D illustrate an overlap joint 13a, an angled overlap 13b, a step joint 13c, a butt joint 13d reinforced by plug 11, and a tapered joint 13 of FIG. 2, respectively. The taper 13 may slope either way; the catheter body 16 may be bonded to the inside of the optical shield 12 as well as to the outside. In addition, joint reinforcing material wire wrapping 13f, thread wrapping 13g, and a metal or plastic band 13h may be used. Bonding agents for joints 13a-d include epoxy, cyanoacrilics, and friction fit using shrinkable or compressible catheter material. Any joint and any reinforcing material may be used in combination with any optical shield design. As shown in FIG. 1, a thin coating material 17 such as fluorocarbon, hydrocarbon, or silicone polymer may be put on the exterior distal end of the shield to minimize sticking of the optical shield 12 to tissue 34, to reduce adherent char, to reduce biological interactions between blood 36 and the optical shield 12, and to reduce Fresnel reflections.

Various methods may be used to fabricate the optical shield 12. The shield may be free formed from tubing in a torch or other heat source using glassblowing techniques. It may be formed over a precision mandrell using heat. Or, as shown in FIG. 8 it may be assembled from two parts by fusing and bonding the parts. In FIG. 8A a rod 600 or disc with the polished end is inserted into a tube 602. Typical dimensions are indicated but any size may be made.

In FIG. 8B the tube 602 and 600 rod are fused with a torch $CO_2$ laser or other heat source. If a rod is used, the excess rod is cut off as in FIG. 8C and the assembly is polished on the distal end. The assembly of FIG. 8D thus provides an optical surface both inside and outside. It may be further shaped as in FIG. 8E.

Figure 9A:
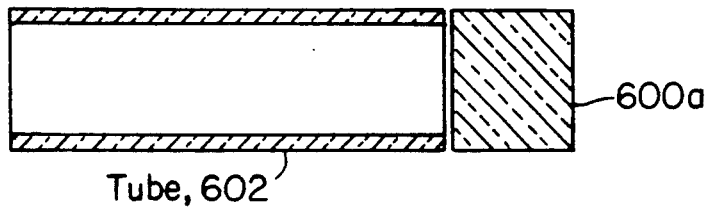
Figure 9B:
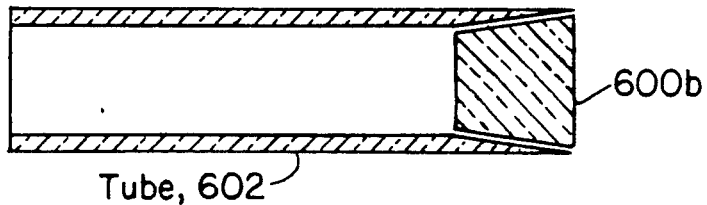
Figure 9C:
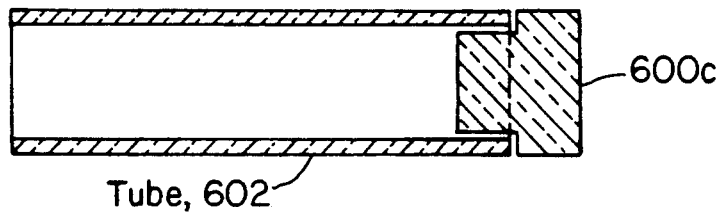
Figure 9D:
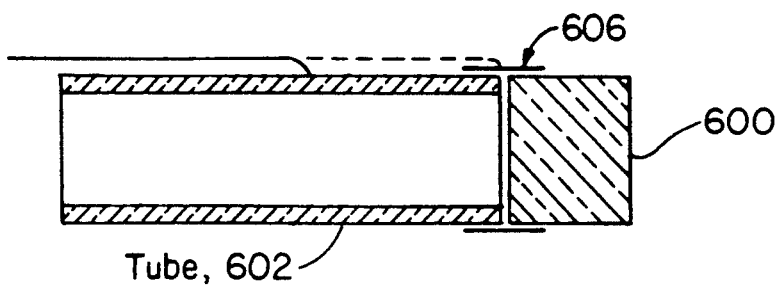

An alternate construction is shown in FIG. 9 wherein the rod or disc 600a is attached to the tube 602 using a butt joint as in FIG. 9A. Matching conical surfaces for rod or disc 600b and tube 602 FIG. 9B will help keep the joint away from the laser beam path 29c of FIG. 4. Alternatively a step diameter in the rod and plug 600c, FIG. 9C, will help to do the same. A metal band 606 can be used to bind and strenghten the joint as in FIG. 9D.

Other embodiments of plug 11 holding optical fibers 20 are shown in FIGS. 10A-G. A piece of solid material can be drilled with parallel holes to make a straight array plug 11a, or holes may be angled 11b; these holes are skewed so as not to intersect inside the plug. Optical fibers 20 may be bonded with epoxy or other bonding agent 19a,b in the holes in the plug, with distal ends 28a,b optically finished. When the optical fibers are finished separately from the plug they may be recessed or protruding, or the bonded optical fibers 20 and plug 11, 11a, 11b may be optically finished as a unit. Optical fibers 20 may be optically contacted or fused to transparent plug 11c, FIG. 10C, or embedded in the plug 11d, FIG. 10D. Preferably the transparent plug 11c,d will have the same thermal expansion properties as for the optical fibers 20, to minimize stress at the joint. Melting temperatures need not be the same, however, as it may be desirable to form the plug 11c, 11d around or in contact with the optical fibers 20, without melting the fibers. The junction 28c, 28d between optical fiber 20 and transparent plug 11c, 11d must be of good optical quality. Plug 11e in FIG. 10E shows the optically polished 28e. This construction is similar to that of the molded epoxy plug 11 of FIG. 2. Similarly, in FIG. 10F the optical fibers 20 may themselves be fused together with or without the addition of a fusing or sintering material 19f to form plug 11f with optically polished surface 28f. FIG. 10G shows optical fibers 20 fused to each other with optional fusing material 19f, with their output ends 28g fused, bonded or optically contacted directly to optical shield 12g. In this case the thickness of the distal end of the optical shield 12g is adjusted to allow the proper divergence of the emitted laser beam 29g, to obtain the correct beam spot size 27g on the distal face of the optical shield 12g. A similar arrangement can be used for transparent plugs 11c and 11e in bonding or fusing them directly to the optical shield 12g.

When, as in FIG. 1, there is an intervening space 25, between the plug 11 and the optical shield 12, it may be filled with air. Alternate embodiments may have this space 25 evacuated, gas filled, or transparent-fluid filled to reduce Fresnel reflections. Optical fibers 20 and optical surfaces adjacent to this space may be coated with an anti-reflection coating 25a,b to reduce Fresnel reflections.

Alternate embodiments of the catheter body material 16 include plastic, plastic with "memory" or an ability to retain deformations, metal tubing, corregated or spiral for flexibility, and coated versions of the above for biological compatability. A mesh or metal, glass, or plastic fiber may be incorporated into the catheter body 16 so as to enhance control. For example, "torque control" will make the catheter body 16 flexible to a bending motion, but it will resist twisting when torque is applied. This allows the laser catheter 10 to follow bends in a vessel, but the distal end may be rotated by rotating the proximal end of the catheter body 16.

An alternate embodiment of proximal input array 46 is shown in section in FIG. 11A. Optical fiber ends 20a-h are secured by clamps 206 arranged in a circular array 46a, and selection is performed by rotating the array 46a on the laser beam, about an axis 47. Another embodiment, shown in FIG. 11B, has the optical fibers at the proximal end 40a-c'' arranged in the same spatial array 46b as for the distal end, with each optical fiber 20a-c' in the same relative position at both ends. Central fiber 40a is surrounded by first ring 40b—b'' and second ring 40c—c''. Such an arrangement of optical fibers is termed a "coherent bundle" by accepted terminology. Square packing or other arrays may be used in coherent bundles. Any number of rings may be used. Another embodiment has optical fiber 20 ends pointing inward on a ring 108, as shown in FIG. 12a,b.

Alternate embodiments of optical fibers 20 include any light conduit. The optical fiber described previously has a core 22 which carries the optical radiation, a cladding 24 of lower index of refraction which confines the radiation, and a jacket or buffer 26 which protects and strengthens the optical fibers 20, FIG. 2. Alternate embodiments include optical fibers 20 without buffer 26, and without buffer 26 or cladding 24. (In the case of core only the surrounding air or gas functions as lower index cladding.) Graded index optical fibers may also be used. The core 22 need not be solid; a fluid filled tube may also be considered an optical fiber 20. A gas or air filled hollow waveguide tube may also be used, and may be made of metal, glass or plastic, with an optional reflective coating inside. Various numbers of optical fibers may be used. In the preferred embodiment, nineteen optical fibers 20 form a symmetric hexagonal close packing array as shown in FIG. 1A. This is likewise true for the seven optical fiber 20 configuration shown in FIG. 3. The sequence for larger numbers of optical fibers is thirty-seven, sixty-one, etc., to form hexagonal close packing. The optical fibers need not all be the same size or type in a laser catheter.

A fiber optic bundle, which consists of two or more optical fibers mechanically bonded at each end, may be used instead of any of the individual optical fibers 20. A coherent fiber-optic bundle, which is a bundle of optical fibers with both ends bonded so as to hold the optical fibers in identical or well defined spatial arrays, may be used in place of any or all optical fibers 20.

One alternative embodiment of the laser catheter 10, incorporates a single coherent bundle of optical fibers composed of hundreds to tens of thousands or more optical fibers. Illumination of the proximal input end of the laser catheter 10 will then provide corresponding output at the distal end. Changing the number or area of optical fibers illuminated at the input end will change the spot size at the output end. Moving the input spot will shift the output spot location accordingly. The output beam may be smoothly moved across the target tissue. An output beam which can provide complete overlap is thus provided. Likewise, diagnostic radiation can be supplied to any location, and the return fluorescence or scattered light from the tissue can be monitored at any location. This embodiment is similar to the preferred embodiment described, except that the few optical fibers 20 are replaced by many optical fibers, and the proximal input end has the coherent bundle of optical fibers in a matching spatial array 46b, as shown in FIG. 11B, rather than in a linear array.

An alternate embodiment of the mode mixer is shown in FIG. 6. Optical fiber(s) 20 is clamped between two rigid blocks 136a, 136b, with one or both blocks being transparent. An optional metal reinforcing plate 137a,b may be used to increase stiffness. Several screws 138 pass through plate 137a,b and/or blocks 136a, 136b. Compliant pads 134a,b, having integral projections 133 are disposed between the blocks 136 a and b. These projections cause microbends in the optical fiber(s) 20 when the screws are tightened. One of the pads 134 may be transparent so as to view the light escaping from the microbends in optical fiber(s) 20. Adjustment of screws 138 enable variation of the amount of mode mixing. The optical fiber(s) 20 and pads 134a,b may be cast in epoxy or other bonding material for permanent mode mixing.

Figure 13A:
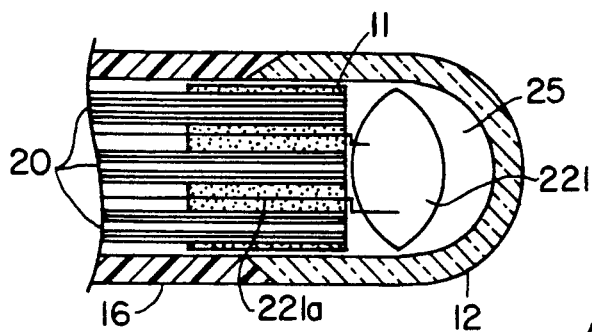
Figure 13B:
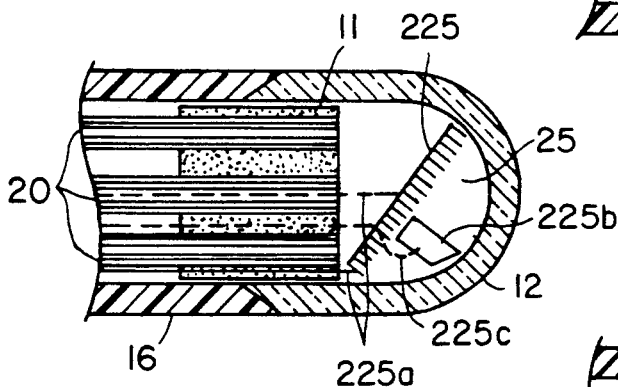
Figure 13C:
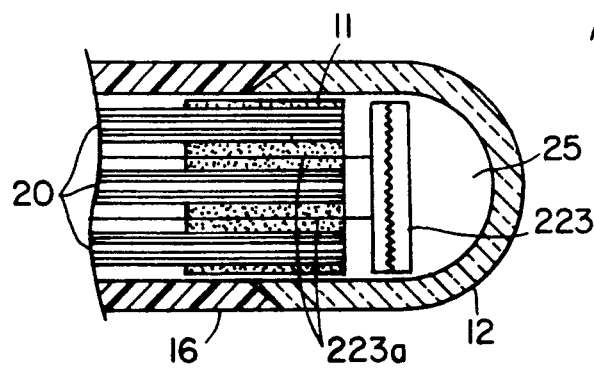
Figure 13D:
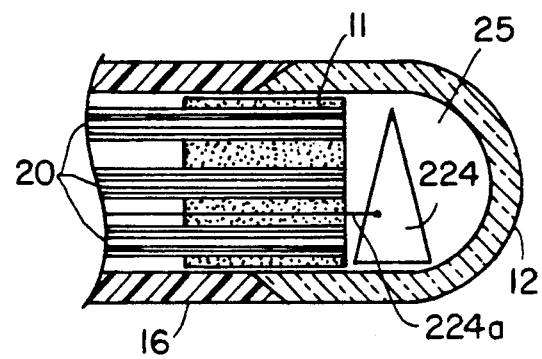
Figure 13E:
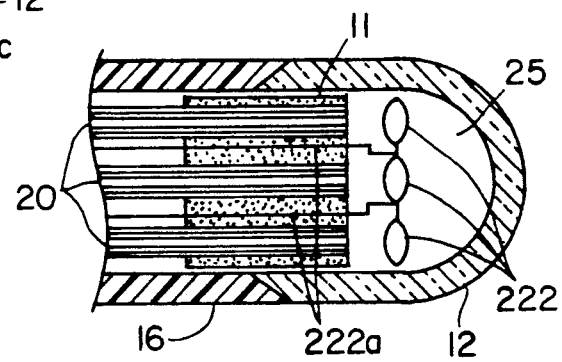

Alternate embodiments of the distal end laser catheter FIGS. 13A-E use a lens 221, multiple lenses 222, holographic element, polarizer, or grating 223, prism 224 or a mirror 225 to control the location and divergence of the laser light and return fluorescence or scattered light. These optical elements shown in FIGS. 13A-E may be fixed or capable of translation, rotation, or tilt, so as to move the position and direction of the existing laser beam. Reflecting surface 225 is tilted, rotated, or translated by control wires 252a. The plug 11 might also be rotable. Prism 224 is rotated or tilted by one or more control wires 224a. Lens 221 is translated in the axial direction by longitudinal motion of control wires 221a, which changes the spot size 27 and beam divergence 29 of FIG. 1. Rotary motion of control wires 221a translates lens 221 perpendicular to the axial direction, and moves the spot position 27 on the optical shield 12. Multiple lens assembly 222 may be translated or rotated with control wires 222a. Holographic element 223 may be translated or rotated with one or more control wires 223a. When the various optical elements are fixed, control wires need not be included in the laser catheter. The mirror 225 may also be controlled by an electromechanical device 225b, affixed to the mirror 225 and the optical shield 12, as shown in FIG. 13B, or the mirror 225 may be affixed to the plug 11. Devices 225b may comprise a piezoelectric, electromagnetic, magnetostrictive, or bimetallic thermal device. Power for device 225b is supplied by wire 225C.

Figure 13F:
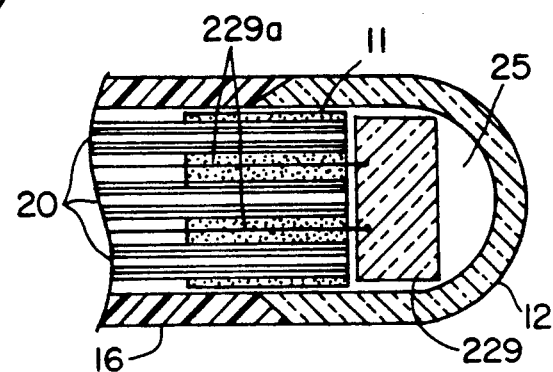
Figure 13G:
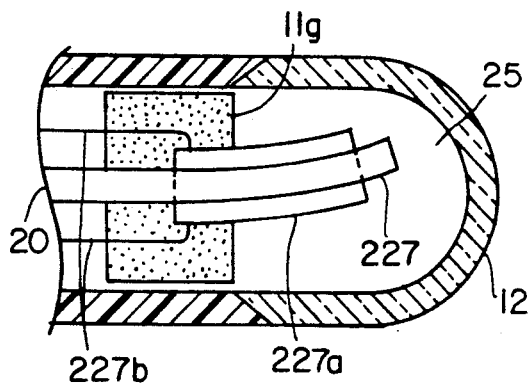
Figure 13H:
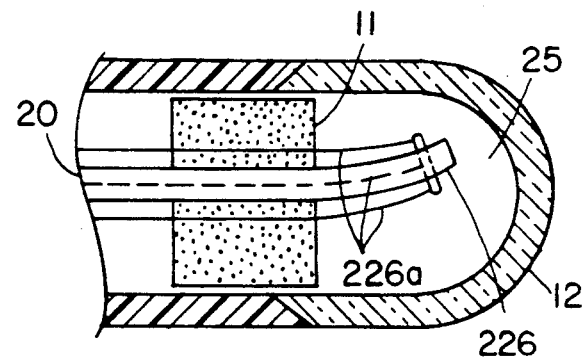
Figure 13I:
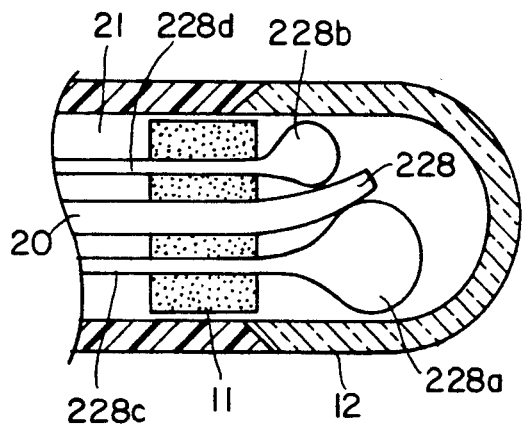
Figure 13J:
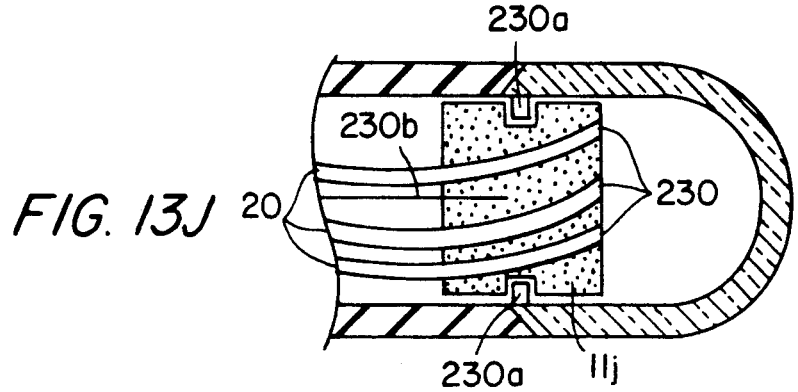

Laser beam deflection may also be achieved by an electro-optic or acousto-optic device 229 as shown in FIG. 13F. Light emerging from optical fiber(s) 20 passes through one or more such devices 229 which are powered by wires 229a; these devices affect the direction of propagation of light when energized. The direction of light emerging from the optical fiber 20 may be changed by mechanically moving the distal end of the optical. One or more control wires 226a, shown in FIG. 13, are affixed near the distal end 226 of optical fiber 20. Longitudinal or rotary motion of these control wires 226a will change the position of the distal tip 226. Electromechanical devices 227a, FIG. 13G may also be used to deflect the distal end 227 of the optical fiber 20, wires lumens 228 c,d in central lumen 21. Central lumen 21 may also be used to inflate balloon(s) 228a,b. As shown in FIG. 13I, balloon 228a is inflated more than balloon 228b, deflecting fiber tip 228.

FIG. 13J shows optical fibers arrayed asymmetrically in plug 11j with the distal ends 230 angled towards one side of the longitudinal axis of the laser catheter 10. The plug 11j may be fixed, or may be allowed to rotate within rotary joint 230a. Control wire 230b applies torque to plug 11j. Rotary joint 230a may be deleted, leaving the plug 11j free to both rotate and translate longitudinally.

The optical elements may occupy the space 25 between the optical fibers 20 and the optical shield 12, or they may be incorporated into the shield 12 such as by making it lens shaped, or they may be incorporated into the optical fibers 20, such as by means of graded index lenses at the distal ends, or by physically shaping angled or lensed ends of the optical fibers 20. The plug 11 may be polished in an angled or nonplaner manner to refract the light. The thickness of the optical shield 12, i.e. the distance measured in the axial direction, can be used to control the amount of divergence of the laser light when it reaches the output surface of the optical shield 12. By making the surfaces curved instead of flat the optical shield 12 may also be made to act as a lens. The input surface curvature of the optical shield 12 may or may not match the curvature of the polished surface of the plug 11. In the case of matching surfaces, both surfaces may be polished to appropriate accuracy and optically contacted, as shown by the contact line 28g in FIG. 10G. Such a construction greatly reduces Fresnel reflections from the optically bonded interface 28g.

If not optically contacted, the intervening space 25, FIGS. 1,2 may be filled with a transparent gas, liquid or solid material, as shown in FIG. 1 by the numeral designation 25d. This transparent gas, for example, may comprise an inert gas, such as argon, selected to withstand the high power of the laser radiation traversing it. The filling material may be chosen to match the index of refraction of the optical shield 12 and the optical fibes 20 held in plug 11. The mating surfaces of the plug 11 or the optical shield 12 may be curved, in which case a filling material 25d with a non-matching index of refraction can be provided. The fill material 25d in such case forms a lens which will displace or deviate the laser radiation. The focal length of such lens may be either positive or negative, depending on both the curvatures of the surfaces and whether the index of refraction of the filling material is higher or lower than that of the fiber cores 22 and optical shield 12.

The laser catheter 10 may be used in combination with a guide catheter 140, FIG. 14. The guide catheter 140 is first inserted in the artery 30 of FIG. 4, and brought near the lesion 34. Next, the laser catheter 10 is inserted coaxially within the guide catheter 140 and brought in contact with the lesion 34. A channel 142 (FIG. 14) may be incorporated into the wall of the guide catheter 140. This channel 142 may be used for purge and suction. The annular space 144 between the guide catheter 140 and the laser catheter 10 may also be used for purge and suction. A guide wire 150 may be inserted into the channel 142. The guide wire, which slides independently of the guide catheter 140, helps to position it in the artery 30. A second channel (not shown) adjacent and parallel to channel 142 allows for both purge and suction and a guide wire at the same time. A balloon 146 can be inflated through a lumen (not shown), similar to lumen 142, to stabilize the guide catheter.

A guide wire 150 incorporated into the laser catheter 10, FIG. 15, will aid in positioning the catheter. Lumen 152 containing guide wire 150 is parallel to lumen 21 of the laser catheter body 16 which contains the optical fibers 20. The same lumen 152, or an additional adjacent lumen (not shown), can be used for suction and purge. When the guide wire 150 is in place, the laser catheter 10 may be both advanced and rotated around the guide wire. If the distal opening 154a for the guide wire 150 is proximal to the plug 11, rather than adjacent to it as in FIG. 15 then a more streamlined and smaller catheter body 16 can be used. The guide wire 150 may also be hollow, for suction or purging, or may have balloon 158 affixed to it. The guide wire 150 may also pass through the modified optical shield 12g through opening 154b, as shown in FIG. 16. This opening 154b is sealed to plug 11 so that fluid cannot enter annular space 25 between optical fibers 20b—b' and optical shield 12g. An optional inner tube 155 affixed to plug 11 will provide a lumen 158 for the guide wire, separating it from the optical fibers 20b—b'. An optional sliding seal 156 located on plug 11 or modified optical shield 12g prevents fluid from entering the catheter body 16. The optical shield 12g may be solid eliminating space 25g. The guide wire 150 need not be centered. An off-center guide wire 150 will allow rotary motion of the laser catheter 10 as an aid in positioning it.

Figure 17C:
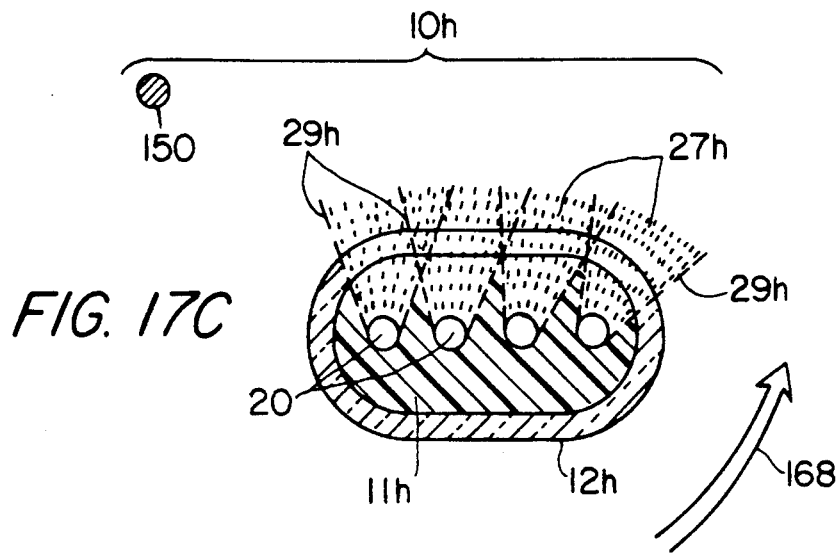

In the above embodiments an off-center guide wire 150 allows improved flexibility in positioning the catheter compared to a centered guide wire or no guide wire. In another alternate embodiment the laser catheter 10 is designed primarily for rotary motion and pivots about the guide wire 150, advancing into the tissue in a helical motion. As such, the rotating laser catheter 10 of FIGS. 17A-D is asymmetrical and designed to cut tissue in one direction. Laser light 29h emerges at an angle to the axis of the lumen. The oblong optical shield 12h, shown in section in FIG. 17C, is the preferred embodiment, but it is not restricted to this shape. This is likewise true for the linear array of optical fibers 20 held by plug 11h. The optical shield 12h contains a reflective or refractive element to change the angle of the light beam 29h emerging from the optical fibers 20. In the preferred embodiment a prismatic surface 164 has an air space 165 so that the laser light 29h suffers total internal reflection and exits at an angle through the distal end of the optical shield 12h. The surface 164 may also be a mirror.

Figure 17D:
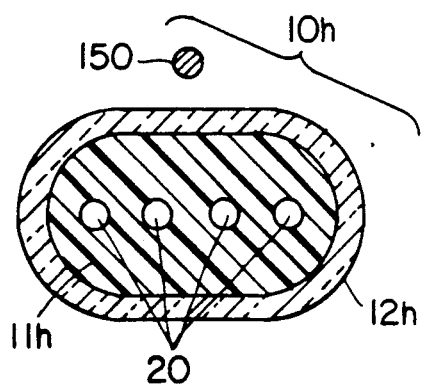

FIG. 17A shows a section through the narrow dimension of the optical shield 12h; FIG. 17B shows a section through the wide dimension of the optical shield 12h; FIGS. 17C, 17D shows a cross section. The location of the guide wire 150 is indicated on all four figures. A bending wire 162 controls the separation between the optical shield 12h and the guide wire 150. Increasing this distance allows the laser catheter 10 to reach tissue farther from the guide wire. Decreasing this distance to a minimum, as shown in section in FIG. 14D, makes the laser catheter more compact for easier insertion. Control wire 162 may be straight for pulling, bent with a rotary joint 167 at the distal end, or a wire, spring, and tube combination which bends when the wire is pulled within the tube. In this embodiment the laser beam 29h emerges through the side of the optical shield 12h, preferably close to the distal end, as shown by laser beam spot positions 27h on FIG. 17B. Thus the tissue removal will be almost entirely on one side. When such diseased tissue is removed the laser catheter 10 is rotated about the guide wire in the direction indicated by the arrow 168 in FIG. 17C until it contacts more tissue to be removed. The optical shield 12h is advanced in this helical path as tissue is removed. The radius of the new lumen formed in the tissue depends on the distance between the optical shield 12h and the guide wire 150 pivot point. The guide wire 150 need not be the only means of pivoting the laser catheter.

An alternate embodiment uses a balloon 166 FIG. 17 A and B, to provide an anchor point. If the balloon 166 is proximal to the optical shield 12, then the laser catheter 10 can be positioned using deflecting wire 162, without using a guide wire 150. The balloon 146 can be incorporated into the guide catheter 142, and the laser catheter 10 rotated inside it. Similarly, a balloon 146 which is inflated asymmetrically affixed to either the guide catheter 142, or the laser catheter 10, will position it. A balloon 176 on a rotary joint, shown in FIG. 18, will allow rotation of the laser catheter 10 without it shifting. An annulus 173 is cut into catheter body 16, and sleeve 174 in one or two parts is installed in the groove. Balloon 176 is attached to the sleeve 174, which has a ring of openings 175 to allow fluid to flow from lumen 172 to inflate the balloon. The fluid will also lubricate the annular space 173 between the sleeve 174 and the catheter body 16, allowing easy rotary motion. An alternate embodiment of this laser catheter 10 for helical cutting uses an asymmetrical optical shield 12d shown in FIG. 7D.

An alternate embodiment of this laser catheter 10, not shown, designed for rotary cutting, utilizes two or more identical optical shields 12h spaced symmetrically around the guide wire 150. The proximal end of the rotating catheter may be mounted on a rotary stage so as to avoid accumulated twist in the catheter body 16.

V.A.4. Optical Input System

FIGS. 12A, 12B, 19, and 20, illustrate fiber selector system devices useful in connection with the invention. FIG. 19 is a system in which the positions of the laser 92 and a shutter 44 and lens 41 are all fixed, and the optical fibers 20, typically an arrangement of 7 or 19 of them, are mounted on a holder 46 in a linear array 46 and translated by mechanical translator 200 in one dimension in front of the focal point of the lens 41. The optical fibers 20 are mounted in the array either by a mechanical clamp, which may be provided with a set of groves to seat the fibers, or they may be glued between two glass slides and this assembly then clamped as a unit on top of the translator 200. The translator system consists of two small hand-operated mechanical stages which bring the fiber array to the correct elevational position and focus in front of the focal point of the laser. The third translational stage is electrically operated by a motor 204 and computer 80. This stage translates the array of fibers 46 as in FIG. 19 along the horizontal dimension such that one fiber after another is brought to the focal point of the laser.

Such mechanical translators may be obtained from Klinger Scientific, New York. Electrically operated translators are available from Aerotech Corporation. Pittsburg, Pa.

Prior to actual use, the stopping positions of the translator must be properly set. The procedure used is to translate the array of fibers, with the laser set to low power operation, to determine if the fibers are properly aligned. The motor driven translation stage has an optical encoder which allows the computer to monitor the position of the stage at all times. Once properly aligned, the computer stores the location of each particular fiber, and then each fiber can be assigned a position and the computer can rapidly access any one of these fibers, or it can be instructed to repeatedly step from one fiber to another in any desired sequence and for any desired time duration.

The operation of shutter 44 controlled by computer 80 determines the amount of time each fiber 20 conducts the optical radiation to the tissue. In actual use it is essential that the laser be turned off when the fibers are being moved, because if high power laser radiation falls on the fiber cladding or any other part of the system damage may result. Thus, for example, 100 um core optical fiber must be brought into proper position with an accuracy of approximately 20 micrometers before the shutter is opened and the laser light is allowed to enter the fiber.

A photodiode 45 mounted near the input ends 40 of the optical fibers 20 can detect scattered light, either from the input ends or from the cladding 24. Minimum scattered light indicates the best alignment. This signal from the photodiode 45 can be coupled to the computer 80 to cause the computer to overload the motors 204 to reposition the fibers to optimize the coupling of laser light 94 into the input ends 40. It can also serve as a continuous monitor during operation, providing feedback to computer 80 for small corrections in optical fiber array 46 position. In this case all three axes of translation stage 200 should be motorized. A laser power meter 452 can also be used for automatic alignment. It is placed at the distal end of the laser catheter 10 and connected to the computer 80, or it can monitor extra optical fiber 20d, not incorporated into catheter body 16. The computer 80 adjusts the input ends 40 for maximum power transmission.

A photodiode or photomultiplier 64 can monitor scattered return light at the laser wavelength, as shown in FIG. 21. Failure of optical fiber 20 or optical shield 12 will scatter laser light 94, which returns 54 through optical fiber 20 and is detected by detector 64 connected to the computer 80, which closes shutter 44, FIG. 19.

The shutter 44 is a mechanical shutter similar to that used on a camera, except that it is electrically driven and is activated by the computer. When a rapid sequence of exposures is desired, such as on a millisecond time scale, the computer 80 closes the shutter 44 and causes the motor 204 to move the translator 200 to a new position, bringing a new fiber into alignment. The shutter is then opened by the computer, allowing laser light to enter the selected fiber. The shutter exposure time is predetermined and programmed in the computer. An attenuator 47 is placed in the path of the high power laser beam 94. This contains Fresnel reflection plates with adjustable angles which vary the amount of attenuation of the laser beam. An alternate embodiment uses a half-wave plate, followed by a polarizer, as an attenuator 47. Rotation of the half-wave plate rotates the polarization and changes the amount of laser light 94 which passes through the polarizer.

FIG. 20 shows an alternate embodiment for coupling laser light into the optical fibers. In this case the light beam is moved by the translator 200, rather than the fibers 20. In this way the fibers, which are still in a linear array, are selected by moving a mirror 48 which is mechanically fixed in holder 204 in spaced relation to lens 41'. Shutter 44 turns off the laser, as in FIG. 19, while the alignment is being made. Also, the shutter operation and translation of the holder are controlled by a computer driven motorized system. An alternate embodiment shown in FIG. 12A and 12B, uses a rotary system for positioning the laser beam 94 instead of a linear translator. In this system the optical fibers 20a-h are arranged in on a circular holder 108 by clamps 206. The holder is concentric to the motor shaft 104 of a galvonometer scanner, motor, or stepper motor 102. A mirror 98 is mounted on this shaft at a 45° or other angle to the shaft axis. The optical radiation from laser 92 is focused by lens 41 on mirror 98. As the shaft 104 is rotated the beam of focused light is reflected onto different points on the circle and enters different optical fibers 20, depending on the rotational angle of the shaft 104. Although the optical fibers 20 are shown evenly spaced all around the holder 108, they may also be closely spaced on an arc, in an array similar to linear array 46.

An alternate embodiment uses an acousto-optic or electro-optic deflector 49 of FIG. 19 to steer the laser beam to the input ends 40 of the optical fibers 20. Optical fiber holder 46 remains stationary and the computer controlled acousto-optic deflector 49 directs the laser beam 94 to the appropriate optical fiber 20. A two dimensional acousto-optic deflector 49 will allow input ends 40 to be arranged in a two dimensional array.

V.A.5 Spectral Detection System

While catheter techniques have been used for many years to access vascular atherosclerotic sites, diagnosis of these lesions has remained indirect, the standard method being x-ray visualization of the vessel lumen with radio-opaque dye. By employing optical fiber catheters, in accordance with the invention, spectroscopic methods to diagnose in situ plaque deposits is possible. Percutaneous methods for evaluting atherosclerotic lesions are of considerable interest, and are particularly valuable for therapies employing laser ablation.

A generalized spectral system is shown schematically in FIGS. 21 and 22. Excitation light 95, FIG. 21, from a laser or conventional light source is sent into a selected optical fiber 20. The excitation light 95 should be of sufficiently low power so as not to injure the tissue 34 of FIG. 4 to be analyzed. This light passes through a beam splitter 52 or a mirror with a hole 50, FIG. 22. It is focussed onto the input end 40 by a lens 41. The light exits the distal end of the optical fiber 20, passes through the optical shield 12, and impinges on the tissue 34 of FIG. 4. The fluorescence and scattered light is returned via the same or a different optical fiber 20 to the proximal end 40 of the optical fiber 20. This return light 54 is separated by the beam splitter 52, which may be of the polarizing type, or by the mirror 50 with hole 51 (FIG. 22). This return fluorescent or scattered light 54 enters a spectrum analyzer 60.

FIG. 23 is a schematic of one type of spectral detector 65 which may be desirable to use with this system and which can detect many different wavelengths simultaneously. A diffraction grating 68 which disperses the return light from a target. The dispersed light is projected onto a multichannel detector 70 which has many detectors, each one of which corresponds to a single wavelength of light leaving the grating 68. In this manner the entire spectrum of the return light may be obtained in a very brief time because all wavelengths are collected simultaneously.

A typical type of detector 70 is an array of photodiodes. An optical image intensifier may be provided in front of the array, if the light signals are weak. The photodiodes convert light photon signals into electrical currents. The array of diodes may be coupled to an automatic electronic scanning device that samples each of these diodes briefly. This spectral information is then fed into computer 80 and can then be shown in a display 86 of the intensity of light at each wavelength or by comparison to some previously stored spectrum.

The correlation with a previously stored spectrum may be used to determine whether the spectrum of the return light is similar to the spectrum of plaque or of arterial wall or of some other type of tissue, and the resulting comparison may be displayed on a numerical display 84.

Alternatively, detector 70 may comprise a plurality of colored glass or interference filter elements, rather than a diffraction grating. The filters are selected to correspond to particular wavelengths where a large discrepancy is observed between the light from healthy arterial wall tissue compared to that of plaque. A more detailed description of a preferred embodiment of a computer controlled spectral detection system will be given later in connection with FIG. 24.

V.B Control System

V.B.1. Spectral Diagnostics

V.B.1(a). General Methods

Visual diagnosis of suspected atheromateous arterial lesions, both inside the body and in excised tissue, usually requires histological confirmation. Normal and diseased tissue are often rather similar to the eye, and visual clinical judgements are based on subtle impressions from texture, color and other factors which are often difficult to quantify. Visual diagnosis through the narrow lumen of a blood vessel using a fiber optic imaging bundle is particularly difficult, since the field of view is greatly restricted and visual impressions can be distorted.

The method of spectroscopic visualization, which is the subject of this part of the invention, is a powerful new adjunct to visual methods. As previously indicated, this method is based on the fact that normal and diseased tissue of a given type, as well as tissues of different types, all exhibit distinct spectroscopic features. These characteristics can often differ dramatically, enabling a diagnosis to be performed rapidly and accurately.

Spectroscopic characteristics are obtained by illuminating the portion of the tissue to be diagnosed with optical radiation, either from a conventional source or a laser, and collecting and analyzing the returning spectroscopic signal. Either pulsed or continuous optical radiation can be used.

Any of a number of characteristics can provide spectroscopic signals useful for distinguishing tissue type or tissue condition. The spectroscopic phenomena of reflection, elastic and inelastic scattering including Raman scattering, absorption and fluorescence can all be used to diagnose tissue. A pulsed source can yield fluorescence, the decay time (lifetime) of which can be different for various tissue types or conditions. Short optical pulses can also provide distance (ranging) information. Pulses of accoustical radiation, propagating along an appropriate fiber conduit, can also be used for ranging. Further, selective staining of tissue plaque can be used to enhance spectral distinctions betwen different types of tissue. The detection system can remain in operation while the intense laser beam removes tissue, providing real-time diagnostics. Continuous monitoring enables rapid detection of changes such as would occur when a plaque-arterial wall boundary is encountered. After the diseased tissue is removed, the system can perform diagnostics on the excised area. Although the above example illustrates use of this method for atherosclerosis, it should be of general applicability for in vivo medical use.

Various types of illumination may be applied to the area to be diagnosed. Light from conventional sources may be used broadband, or it may be filtered or dispersed before being directed into the fiber. Likewise, light from tunable or fixed frequency lasers, either pulsed or continuous may be used. A beam splitter arrangement or the equivalent can be employed if the same fiber is used both to deliver intense light and collect returning light for analysis. The returning light can be filtered dispersed, or detected broadband. Solid state light detectors such as photodiodes can be used to detect the returning light. If high sensitivity is required a photomultiplier detector can be used. Detectors and light sources can be coupled to the optical fibers by mechanical, electro-mechanical, or acousto-optical or other means.

A vidicon, diode array or imaging detector with a dispersing spectrometer can be used to simultaneously collect a broad range of spectral information from a sigle fiber and, as discussed earlier, this data can be used to differentiate types of tissue. Spectra can be displayed, or preferably analyzed by computer, providing a rapid determination of whether the material being irradiated is plaque or healthy tissue. Using this information, the firing of the intense laser can be controlled either by the surgeon or by the computer. When the diseased tissue is removed from this site a nearby fiber will be selected and the process repeated. The same type of computer control should be feasible with many other detection schemes.

Multiple fibers connected to individual diodes, or to a vidicon or imaging detector, can be used to map the distribution of plaque and other tissue at the tip of the catheter. Likewise a single movable fiber can provide similar information. This information map can be stored in memory and the image displayed. The surgeon then has the option either to select the portion of the "field of view" to be irradiated by the intense laser and fire it, or else to let the computer automatically fire the laser at the diseased points on the map. In either case the plaque is selectively removed, leaving the healthy artery wall intact. As tissue is removed the map is continually updated, and the catheter tip then advanced.

The detection systems and fiber optic systems described above are of general applicability to in vivo diagnostics of all types. The application to atherosclerotic plaque is an illustration of a particularly attractive use of a miniaturized fiber optic spectroscopic analysis system.

V.B.1(b). Fluorescence Diagnostic

Experiments in our laboratory establish that fluorescence is a specific spectral diagnostic that can be used to distinguish fiberous plaque from healthy arterial wall. The studies were made on human cadaver carotid artery samples, obtained and examined within 24 hours of extraction. Using standard pathologic classification, all samples used were determined to be fiberous plaque or early atherosclerotic plaque.

Whole arterial wall samples were placed in quartz cuvettes, immersed in saline solution. The lumen side of each sample was secured flush against a face of the cuvette, thus providing a well defined suface from which to observe fluorescence. Sample cuvettes were placed in a Perkin Elmer spectrofluorimeter of standard type. Filters with cutoffs at wavelengths longer than the excitation wavelength were used to suppress background light scattered from the incident beam. Incident power was less than 100 uW, and the beam irradiated an area of 3 mm×5 mm.

Immediately after spectroscopic examination, samples were fixed in formalin. The irradiated area was then isolated and several histological sections made. Standard hematoxilin and eosin staining was performed. The presence or absence of plaque was established from the resulting slides, and plaque thickness was measured for each sample in at least 15 different locations in the irradiated area, and then averaged.

The wavelength 480 nm was found to be a peak for exciting fluorescence, with an excitation width of about 50 nm. Excitation at this wavelength resulted in spectra displaying pronounced differences between normal arterial wall and artery wall with plaque. Typical fluorescence spectra are shown in FIG. 26. Normal artery samples displayed distinct spectral peaks of approximately equal size at 550 and 600 nm (FIG. 26A). Fiberous plaqued artery samples exhibited peaks at the same two wavelengths, but with the 600 nm peak always smaller than the one at 550 nm (FIG. 26B).

We devised a simple procedure to quantify the fluorescence lineshape differences. Using the fact that the height of the 600 nm peak relative to the valley at 580 is much greater for normal than for plaqued artery, we defined the contrast ratio, $R = I(600)/I(580)$, with $I(\ )$ the fluorescence intensity at wavelength Contrast ratios were obtained for six histologically determined samples. The values for three normal samples ranged from 1.72 to 2.00, whereas the values for three samples with plaque thickness greater than 0.5 mm ranged from 1.03 to 1.09. At test comparing these two groups yielded a P value of less than 0.01, confirmimg that fluorescence can distinguish between normal artery and artery with a plaque which is 0.5 mm or more in thickness. We thus conclude that fluorescence induced by 480 nm exciting light is a an effective spectral diagnostic for the laser catheter invention described herein.

V.B.2. Tissue Removal Dosimetry

Laser catheters designed in accordance with the principles of the invention have been constructed in our laboratory and used to study various features of the invention, including determining the degree of control in the tissue removal process. Both single fiber and multiple fiber laser catheters have been constructed.

FIG. 27 depicts one prototype studied. In this prototype a single optical fiber 20 with a carefully cleaved or polished output tip 23 was rigidly centered inside a transparent optical shield 12. The fiber 20 had a 133 um core diameter and a numerical aperture of 0.21. The optical shield 12 was formed by a length of 0.5 mm thick quartz tubing of 3 mm outer diameter, closed at one end with a torch to form a hemispherical output surface. The laser beam 29 emerging from the distal end 23 of the optical fiber 20 produced a distribution of light in the form of a circular spot 27 on the outer surface of the optical shield. The spot size, defined as the diameter at which the intensity of the spot decreased by half, was adjusted by choosing the appropriate distance between the tip 23 of optical fiber 20 and the outer surface of the optical shield 12. Reticon measurements showed the beam profile to be approximately uniform across the spot, falling rapidly to zero at the edges. Spot size determinations were accurate to ±25 um.

The experiments used blue-green light from a Coherent I-20 argon ion laser. Data were taken in freshly excised sections of human cadaver carotid artery with fiberous plaque, cut open lengthwise to expose the luminal surface. Samples, typically 1 mm thick, exhibited relatively acellular intimal fibroplasia, often infiltrated by lipid and foam cells, overlaying media. The sample was placed in a petri dish 37 and immersed in either blood or saline solution 36a. As shown in FIG. 27, the tip of the optical shield 12 was brought into contact perpendicular to the luminal surface of the sample, displacing the intervening fluid, and pressed against it with a constant force of one ounce (28 kdynes). Dimensions of holes produced in blood and saline were the same with experimental variability, and so saline was used in most studies. Laser power was measured at the output surface of the device with an accuracy of ±50 mW. Exposure times, controlled by an electronic shutter placed in the laser beam, were accurate to ±2 msec.

Holes formed by laser ablation were roughly cylindrical with rounded bottoms. Hole diameter was measured at the luminal surface of the tissue using a dissecting microscope with eyepiece reticle. Hole depth was measured by using a histological microscope with a calibrated fine adjustment focussing knob, bringing first the tissue surface and then the hole bottom into focus. Measured hole dimensions were accurate to ±25 um.

Each data point was averaged from at least 7 individual holes. Since the full range of variations will be encountered in clinical use, error bars were drawn to encompass all values observed.

FIGS. 28A and 28B plot diameter and depth, respectively, of holes produced using a 750 um spot size at powers of 2.5, 5, 7.5 and 10 W, versus exposure time. There are several important trends. Consider first the curves of hole diameter versus exposure time, FIG. 28A: As exposure time increases hole diameter approaches the spot size. Also, as intensity increases hole diameter approaches spot size more rapidly. As discussed in Sec. V.A.1, knowledge of hole diameter as a function of exposure time for given values of laser power and spot size can be used in the design of laser catheters with multiple fibers to provide a set of spots on the distal end of optical shield 12 of FIG. 4 with sufficient overlap for complete coverage in the tissue removal process.

Exposure times at which 90% of the limiting hole size is reached are 25, 25, 200 and >1000 msec for 10, 7.5, 5 and 2.5 W laser powers, respectively. The 90% diameter is useful because sample-to-sample hole size variations are much reduced at .hits exposure time. It thus represents a practical threshold for producing reproducible holes. Exposure times for which the first perceptible spot of tisue is removed ("absolute" threshold) were found to vary greatly from tissue sample to sample, and are therefore of little clinical value.

The hole depth measurements, FIG. 28B, show that in each case depth increases linearly with exposure time up to the point of perforation. This indicates that the removal rates for fiberous plaque and normal arterial wall are similar. The slope of each curve is the penetration velocity (mm/sec). Note that penetration velocity increases with increasing intensity. The observed penetration velocities are 2.56, 2.43, 1.42 and 1.05 mm/sec for 10, 7.5, 5 and 2.5 W laser powers, respectively.

The data show that by varying laser power and exposure time in an optical shield laser catheter of chosen spot size, one can predictably control hole depth and diameter in the tissue ablation process. Selection of the proper penetration velocity, which can be achieved by choosing appropriate spot size and power, is crucial. An uncontrollable penetration velocity is undesirable because in many cases there is only a small range between the absolute threshold photon dose and the dose leading to perforation of the thin arterial wall. The laser catheter invention described herein provides the needed control for clinical se.

V.B.3. System Operation and Control

FIG. 24 is a block diagram of the entire operating system for removal of plaque in an artery. First, the laser catheter 10 with optical shield 12 is inserted and the shield is brought into contact with the lesion. Next, a determination is made as to the type of tissue at which each optical fiber 20a–c' is aimed. Optical fibers aimed at diseased tissue are selected to deliver high power laser radiation, removing the tissue, whereas those aimed at healthy tissue or blood are not so activated. Thus, selective tissue removal is obtained. The aforementioned spectral diagnostics are used to diagnose the tissue in front of each fiber.

A light source, which may be a laser or conventional source, 98, is applied to the fibers. In the case of a conventinal source, wavelengths should be selected by an optional monochronometer or filters 100. Light is sent through the optical fiber selector 74 to the fiber of choice. The fibers are placed on a mechanical translator previously described in connection with FIG. 19. The translator is controlled by a computer, so that the correct fiber is moved into position in front of the light emerging from the fiber bundle. Alternatively, a rotating mirror 98 as in FIG. 12 or acousto-optic beam deflector 49 as in FIG. 19 may be used to align the light source with the fibers.

The diagnostic light exits the distal end of the selected optical fiber 20a–c', passes through the optical shield 12, and falls on the tissue. The tissue scatters and absorbs the light, and in the latter case re-emits some fraction of this light, usually of a longer wavelength. This light re-enters the distal ends of the various optical fibers 20. The return light may come through the same or a different fiber and is then coupled out by the selector system 74 using, for example, a beam splitter. This light goes to either a monochromometer or a filter system 76 and then is detected by a photodiode, photomultiplier or other detector 64. A rapid scan control 90 moves the grating, or the prism, or whatever spectrum-selective element is used in monochromometer 76, so that it selects one wavelength after another, sequentially. In this way the entire spectral signal from the selected fiber(s) is converted into a time varying signal, which is coupled to computer 80 via the detector 78. Alternately, a multichannel analyzer 65 as shown in FIG. 23 may be used, collecting the entire spectrum simultaneously and coupling it to the computer 80.

The computer stores the information as a spectrum, which is a graph of light intensity vs. wavelength. This can be displayed immediately on the video display 82. Alternately, the spectrum can be compared to an existing spectrum already stored in the computer, and the difference displayed on the spectral display 86. Corrections can be made for the wavelength dependent sensitivity of the instrument. In the case of a pulsed laser source, instead of a continuous light source, a temporal display of the return light can be shown on display 88. Information from either the temporal or spectral display may be compared to standard spectra stored in the computer 80. The comparative data may then be read onto a numerical display 84 to provide a quantative measure of how well the spectral or the temperal behavior of the return light compares to that emitted from plaque, or conversely, healthy arterial wall tissue. It is quite feasible that fluorescence intensities measured at only a few wavelengths can provide adequate information. In this case, an entire sectrum need not be collected.

In the preferred embodiment, the light source 98 is 476 nm radiation from an argon ion laser. The fluorescent light is monitored at peaks 550 and 600 nm, and valley 580 nm when the 600 nm peak is comparable to the 550 nm peak and the 600 nm peak to 580 nm valley ratio is much larger than one, this indicates healthy artery wall. When the 600 nm peak is much smaller than the 550 nm peak and the peak to valley ratio is near unity, this indicates the presence of plaque.

With a multichannel detector and a reasonably fast computer, or with appropriate multiple filters and detectors, it is feasible to gather this information in a fraction of a second. Thus, within a fraction of a second after the low power spectral light source 98 is turned on, either a spectral or numerical display is provided which indicates the type of tissue at which the fiber of interest is aimed. If the tissue is plaque, and it is to be removed, then the fiber selector 74 will align this fiber with the output beam of the high power laser 92. Then the high power laser 92 is turned on (or it may be already on), an appropriate level of power is selected by attenuator 47, and shutter 94 is open for a predetermined amount of time to remove a certain amount of this diseased tissue. Once this event has occurred, the shutter is closed and the high power laser radiation is stopped.

Next, the procedure is repeated for a different optical fiber 20. If the split-second spectral diagnostic again indicates diseased tissue is present, it is quickly removed by the high power laser radiation. If, however, the spectral diagnostic indicates healthy tissue or blood, the high power laser is not sent through that particular optical fiber 20. This procedure is repeated until all the diseased tissue in contact with the distal end of the optical shield 12 is removed. Then the laser catheter 16 is advanced (typically 0.3-2 mm) or repositioned so as to again be in contact with the remaining lesion 34. The above steps are repeated and the laser catheter 10 nibbles away at the diseased tissue, leaving the healthy artery wall 32 intact. In cases in which significant amounts of plaque 34 have diffused into the artery wall 32, the computer 80 criteria are set so that this less diseased tissue is left intact. The laser catheter follows the trail of the plaque, tunneling through it, leaving the artery wall 32 intact.

If the artery 30 makes a bend 31 as shown in FIG. 25, the laser catheter 10 will tend to make contact with the artery wall 32 at the outside wall of the bend. In the illustrated case of an artery totally obstructed by plaque 34, the optical fibers 20a, b, c, b' aimed at the plaque are fired in turn, removing "nibbles" of plaque 35a, b, c, and b'. Optical fiber 20c' aimed at artery wall 32, is not fired. The lesion is removed asymmetrically. Previously, in the straight section of the artery 30, all optical fibers 20a-c' had been fired, making straight lumen 39. But the asymmetric removal causes the lumen to turn and as the laser catheter 10 is advanced, it follows the new lumen 39a around the bend. The artery wall 32 is not irradiated, and so is not perforated.

Figure 4A:
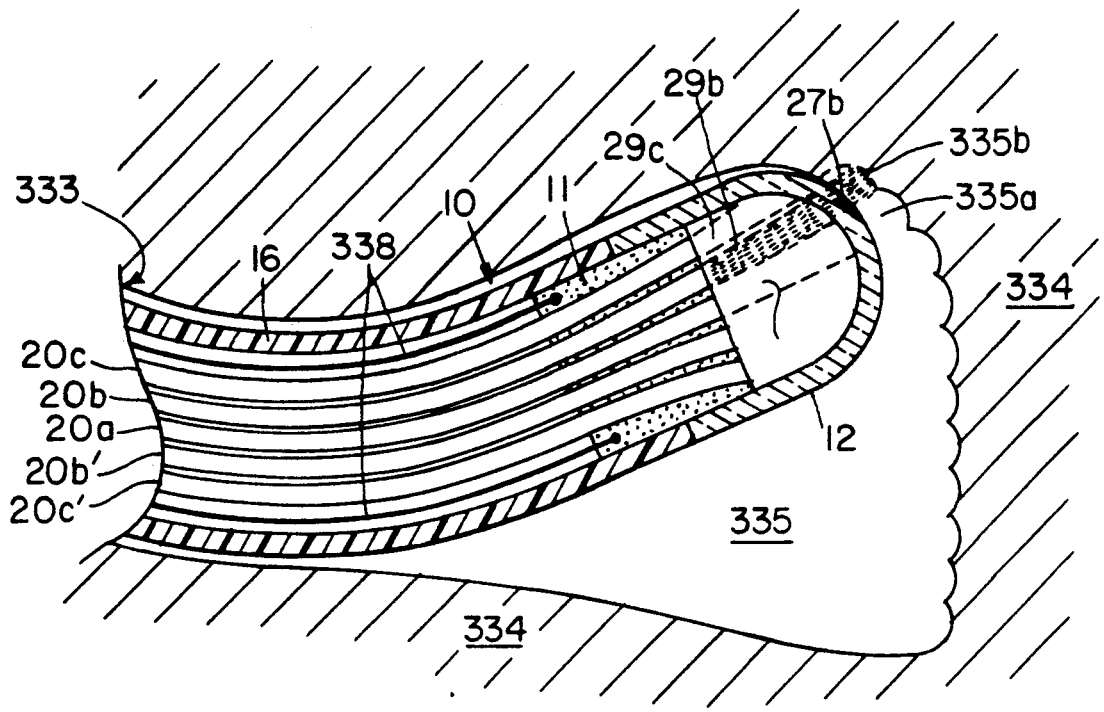
FIG. 4A is a sectional view of the laser catheter of FIG. 4 disposed in tissue.

FIG. 4A represents the laser catheter 10 removing tissue 34 in an artery 30. However, this laser catheter and control system may be used for removing lesions or obstructions, veins, or in any tube, duct, vessel, or body cavity. It may also tunnel through various types of tissue as in FIG. 4A. The laser catheter 10 is in tissue 334, having made or been introduced through, lumen 333. Previous laser firings of optical fibers 20a-c' have removed tissue forming cavity 335. Control wires 338, or electromechanical devices similar to those described in conjunction with FIGS. 13A-J, are used to position the optical shield 12 against tissue to be ablated. As shown, in FIG. 4A, optical fiber 20a has just been fired along beam path 29a, removing nibble 335a from tissue 334. Optical fiber 20b is being fired along the indicated path 29b, removing nibble 335b. Optical fiber 20c is to be fired next, removing more of tissue 334, enlarging cavity 335. Spectroscopic analysis may be performed on each nibble as needed, prior to removal. Optical shield 12 design provides control over spot size 27b and therefore the size of the nibble 335b. It displaces fluids which may accumulate in cavity 335, which can absorb or scatter the laser light. The laser catheter 10 is rotated, advanced or distal end bent by control wires 338 or needed to bring it into contact with additional tissue 334 which is examined and removed as needed. A cavity 335 of removed tissue may be substantially larger than lumen 333 through which the laser catheter is introduced. An alternative design as in FIG. 7F uses semi-rigid tube or cannula 16f with an optical shield 12f. The cannula may be straight or preformed into a curved shape. This may be mechanically to the site of a lesion in any tissue before proceeding with laser treatment or removal of tissue. Such a device is most likely to be useful for smaller lesions.

VI. EQUIVALENTS

This completes the description of the preferred and alternate embodiments of the invention. Those skilled in the art may recognize other equivalents to the specific embodiments described herein, which equivalents are intended to be encompassed by the claims attached hereto.

We claim:

1. A medical laser catheter for removing tissue from a site comprising;
    a catheter having an optical waveguide extending from a proximal end of the catheter to a distal region at a distal end of the catheter;
    a lumen extending within the catheter and defining a central opening at the distal end of the catheter through such that the distal end of the catheter comprises a rigid output surface surrounding the central opening; and
    a laser coupled to the optical waveguide such that laser radiation can be transmitted from the proximal end of the catheter to the distal end of the catheter, the waveguide emitting a diverging output beam of radiation through the output surface of the catheter such that the diverging output beam substantially overlies the output surface surrounding the central opening at the distal end of the catheter.

2. The medical laser catheter system of claim 1 further comprising an optical system at the distal region of the catheter to couple radiation emitted a the distal end of the waveguide to the output surface.

3. The medical laser catheter of claim 1 wherein the waveguide comprises a plurality of optical fibers each fiber spaced at a radius from a central longitudinal axis of the catheter.

4. The medical laser catheter of claim 3 further comprising a retainer at the distal region of the catheter, the retainer securing the distal end of each optical fiber relative to every other optical fiber in a fixed spaced-apart relationship.

5. The medical laser catheter of claim 4 wherein the retainer positions the distal ends of the fibers such that the fibers generate overlapping output spots of radiation at a fixed distance.

6. The medical laser catheter of claim 3 wherein the optical fibers are symmetrically spaced at radius from a central longitudinal axis of the catheter.

7. The medical laser catheter of claim 3 further comprising a selector to selectively couple the laser to any selected group of optical fibers.

8. The medical laser catheter of claim 3 wherein the optical fibers are positioned in a circular array that is concentric about the opening.

9. The medical laser catheter of claim 1 wherein the distal end of the catheter further comprises a distal tapered surface such that a diameter of the distal surface increases proximal to the central opening.

10. The medical laser catheter system for removing tissue from a site comprising:
a catheter having a plurality of optical waveguides extending from a proximal end of the catheter to a distal region at a distal end of the catheter;
a retainer at the distal region of the catheter, the retainer securing a distal potion of each optical waveguide a fixed distance from a distal portion of every other optical waveguide of the catheter, the waveguides being concentrically arrayed about a longitudinal axis of the catheter;
a guidewire lumen extending within the catheter and defining a central opening at the distal end of the catheter such that the distal end of the catheter comprises an output surface surrounding the opening; and
a laser coupled to any selected group of the optical waveguides such that laser radiation can be transmitted from the proximal end of the catheter to the distal end of the catheter, each selected waveguide emitting an output beam of radiation through the output surface of the catheter.

11. The medical laser catheter system of claim 10 wherein each optical waveguide further comprises an optical fiber an optical element at the distal region of the catheter to couple radiation emitted at the distal end of each fiber to the output surface.

12. The medical laser catheter of claim 10 wherein at least one of the optical waveguides comprises a fiberoptic bundle.

13. The medical laser catheter of claim 10 wherein the output surface comprises an optical shield extending over the distal end of the catheter, the opening at the distal end of the catheter extending through the optical shield.

14. A medical laser catheter system for insertion into a body lumen comprising:
a catheter having a plurality of optical waveguides extending from a proximal end of the catheter to a distal region at a distal end of the catheter, the optical waveguides being adapted for transmission of laser radiation through the catheter;
a rigid optical system at the distal end of the catheter, the optical system including an output surface such that light exiting a distal end of each waveguide is transmitted through the optical system output surface;
a guidewire lumen extending within the catheter and defining an opening at the distal end of the catheter through which a guidewire can be displaced such that the output surface is adjacent to the opening; and
a laser coupled to the optical waveguides such that laser radiation can be transmitted from the proximal end of the catheter to the distal end of the catheter, the waveguides emitting an output beam of radiation through the optical system output surface of the catheter.

15. The medical laser catheter of claim 14 wherein each optical waveguide further comprises an optical fiber.

16. The medical laser catheter of claim 14 wherein the optical waveguide comprises at least one fiber optic bundle.

17. The medical laser catheter of claim 14 wherein the guidewire lumen is centrally positioned at the distal end of the catheter.

18. The medical laser catheter of claim 14 wherein the opening for the guidewire lumen is acentrically located at the distal end of the catheter.

19. The medical laser catheter of claim 14 wherein each optical waveguide provides a diverging output beam of radiation.

20. The medical laser catheter of claim 14 further comprising an optical shield at the distal end of the catheter.

21. A catheter for delivering laser energy within a body lumen, the catheter having a proximal end, a distal end and a cross-sectional area and comprising:
a lumen extending through the catheter, the lumen being open at the distal end of the catheter;
an opening at the proximal end of the lumen for permitting fluid communication with the lumen and to permit a guidewire to be received within the lumen;
a plurality of optical fibers extending through the catheter;
an optical shield mounted on the distal end of the catheter and covering the distal end of the fibers, the optical shield having a distal surface defining an emission surface and providing an optical path from the distal end of the fibers to the emission surface;
a distal opening formed through the optical shield in communication with the catheter lumen;
a retainer for holding the distal ends of the optical fibers in optically transmissive relations to the shield to direct light from the optical fibers through the shield and emit light in a divergent beam such that light emitted from each of the fibers may overlap increasingly in a distal direction and such that the overlapping beams emitted by the optical fibers in combination diverge to define an area which is at least as great as the cross-sectional area of the distal end of the catheter.

22. The catheter of claim 21 wherein the catheter has a diameter of about 1.2 millimeters.

23. The catheter of claim 21 further comprising a guidewire.

24. The catheter of claim 21 wherein the catheter has a cross-sectional area such that the catheter can be advanced through a vascular or coronary lumen of a patent.

* * * * *

UNITED STATES PATENT AND TRADEMARK OFFICE
CERTIFICATE OF CORRECTION

PATENT NO. : 5,290,275
DATED : March 1, 1994
INVENTOR(S) : Carter Kittrell, Robert M. Cothren, Jr., Michael S. Feld and Barry Sacks It is certified that error appears in the above-indentified patent and that said Letters Patent is hereby corrected as shown below:

On the cover page, Item[75] please delete inventors name "Barry Sachs" and replace with the correct spelling ---Barry Sacks---.

At column 26, line 37, please delete the word "through".

At column 27, line 17, please delete "potion" and insert ---portion---.

Signed and Sealed this

Twenty-fifth Day of June, 1996

Attest:

BRUCE LEHMAN

*Attesting Officer*     *Commissioner of Patents and Trademarks*